(12) United States Patent
Weiser et al.

(10) Patent No.: US 9,464,456 B2
(45) Date of Patent: Oct. 11, 2016

(54) SYSTEM FOR PROTECTING STORED GOODS

(75) Inventors: Jürgen Weiser, Schriesheim (DE); Daniel Bihlmeyer, Apex, NC (US); Claus Kaiser, Frankenthal (DE); Michael Faber, Schifferstadt (DE); Agustin Izquierdo, Summit, NJ (US); Stefan Schaffert, Bürstadt (DE); Nils Stello, Saarbrücken (DE); Torsten Gröschl, Eppelborn (DE); Udo Schmidt, Saarbrücken (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/128,260

(22) PCT Filed: Jun. 26, 2012

(86) PCT No.: PCT/EP2012/062351
§ 371 (c)(1),
(2), (4) Date: Mar. 18, 2014

(87) PCT Pub. No.: WO2013/000906
PCT Pub. Date: Jan. 3, 2013

(65) Prior Publication Data
US 2014/0190538 A1 Jul. 10, 2014

Related U.S. Application Data

(60) Provisional application No. 61/501,318, filed on Jun. 27, 2011.

(51) Int. Cl.
*E04H 15/34* (2006.01)
*A01F 25/13* (2006.01)
(Continued)

(52) U.S. Cl.
CPC .............. *E04H 15/34* (2013.01); *A01F 25/13* (2013.01); *A01N 25/34* (2013.01); *B65G 1/02* (2013.01); *B65G 2207/40* (2013.01)

(58) Field of Classification Search
CPC .............. A47C 29/006; A61G 10/005; B65D 88/1606; B08B 15/026; E04H 1/1277
USPC .......... 135/90, 93, 900, 156; 55/361, 385.2; 52/63; 454/187
See application file for complete search history.

(56) References Cited

U.S. PATENT DOCUMENTS

| | | | |
|---|---|---|---|
| 969,899 A * | 9/1910 | Partington | ............ E04H 15/04 135/90 |
| 1,801,247 A * | 4/1931 | Hunter | ...................... E04H 6/04 135/120.2 |

(Continued)

FOREIGN PATENT DOCUMENTS

| | | |
|---|---|---|
| CN | 101374413 | 2/2009 |
| CN | 202095310 | 1/2012 |

(Continued)

OTHER PUBLICATIONS

International Search Report, issued in PCT/EP2012/062351, dated Oct. 4, 2012.

(Continued)

*Primary Examiner* — Noah Chandler Hawk
(74) *Attorney, Agent, or Firm* — Brinks Gilson & Lione

(57) ABSTRACT

A system for protecting stored goods in a storage room, having one or more storage constructions formed by one or more pesticide treated nets (30, 31), capable of enclosing the stored goods, where the storage construction further includes a support frame, means for suspending the support frame, means for opening and closing at least one section of the storage construction while the support frame is in a suspended state, and means for avoiding an overall structural collapse if a net gets entangled. The system is particularly useful for the storage of tobacco, coffee, dried fruits, cocoa, nuts, tea, cereals and spices.

17 Claims, 15 Drawing Sheets

(51) Int. Cl.
*A01N 25/34* (2006.01)
*B65G 1/02* (2006.01)

(56) References Cited

U.S. PATENT DOCUMENTS

| | | | |
|---|---|---|---|
| 3,119,358 A * | 1/1964 | Colson et al. | 109/1 S |
| 3,256,931 A * | 6/1966 | Anders | 165/46 |
| 3,481,073 A * | 12/1969 | Yoshida | A01G 9/22 135/120.2 |
| 3,482,585 A * | 12/1969 | Overstreet | 135/121 |
| 3,772,734 A * | 11/1973 | Kimel | A47H 13/00 16/87.2 |
| 4,062,146 A * | 12/1977 | Grossman | A01G 9/22 135/90 |
| 4,335,712 A * | 6/1982 | Trexler | 600/21 |
| RE31,328 E * | 8/1983 | Anderson et al. | 160/354 |
| 4,706,551 A * | 11/1987 | Schofield | 454/66 |
| 4,911,317 A * | 3/1990 | Schloesser | B65D 90/046 220/1.5 |
| 5,259,408 A * | 11/1993 | Guerin | 135/90 |
| 5,494,066 A * | 2/1996 | McMahan | 135/87 |
| 6,132,088 A * | 10/2000 | Suzuki | B65D 90/046 220/482 |
| 6,145,141 A * | 11/2000 | Whittington et al. | 5/414 |
| 6,201,364 B1 * | 3/2001 | Will et al. | 318/466 |
| 6,776,178 B1 * | 8/2004 | Glynn et al. | 135/115 |
| 6,966,937 B2 * | 11/2005 | Yachi et al. | 55/385.2 |
| 7,703,499 B2 * | 4/2010 | Tait et al. | 160/84.01 |
| 8,733,380 B1 * | 5/2014 | Roberts et al. | 135/90 |
| 2004/0004210 A1 * | 1/2004 | Bauer et al. | 256/32 |
| 2005/0012011 A1 * | 1/2005 | Wu | 248/317 |
| 2005/0229483 A1 | 10/2005 | Iwig et al. | |
| 2006/0213546 A1 * | 9/2006 | Mitsui | E04H 15/42 135/121 |
| 2006/0254158 A1 * | 11/2006 | Saller et al. | 52/63 |
| 2007/0277942 A1 * | 12/2007 | Dondlinger | E06B 9/13 160/273.1 |
| 2008/0282652 A1 * | 11/2008 | Wardlaw | 55/385.2 |
| 2009/0246242 A1 | 10/2009 | Leininger et al. | |
| 2010/0064578 A1 | 3/2010 | Karl et al. | |
| 2010/0132245 A1 | 6/2010 | Vestergaard | |
| 2010/0132752 A1 * | 6/2010 | Vestergaard Frandsen | 135/96 |
| 2010/0192998 A1 | 8/2010 | Villers et al. | |
| 2011/0120001 A1 | 5/2011 | Karl et al. | |

FOREIGN PATENT DOCUMENTS

| | | |
|---|---|---|
| CN | 202918730 | 5/2013 |
| FR | 2800772 | 5/2001 |

OTHER PUBLICATIONS

International Preliminary Report on Patentability, issued in PCT/EP2012/062351, dated Jun. 12, 2013.

* cited by examiner

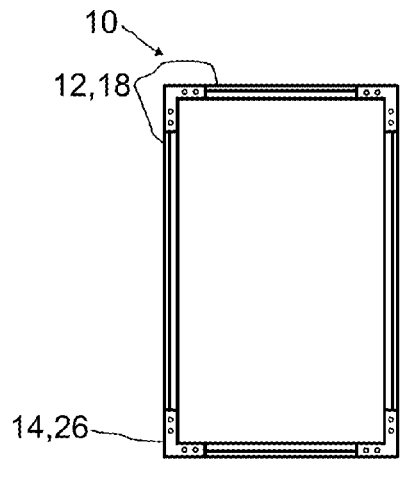
FIG.1a
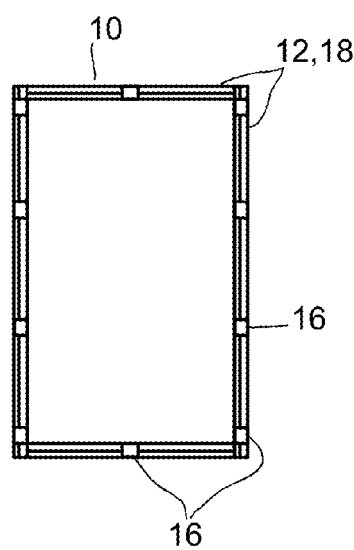
FIG.1b
FIG.1c
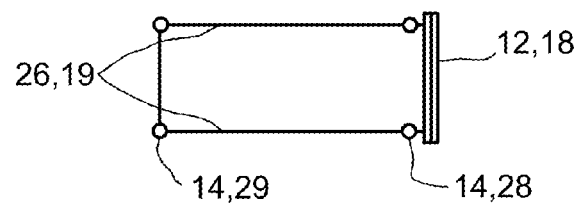
FIG.2a
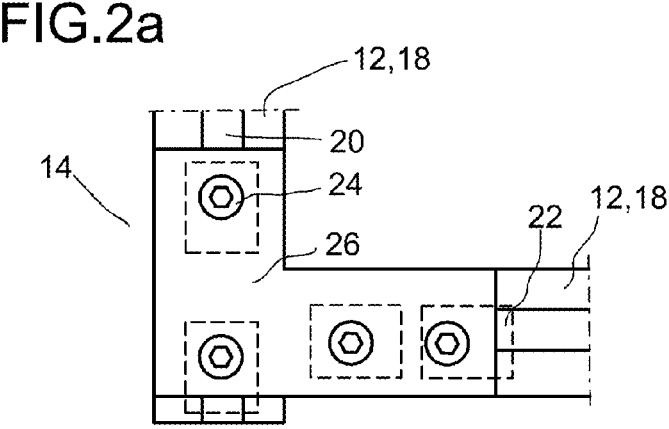
FIG.2b
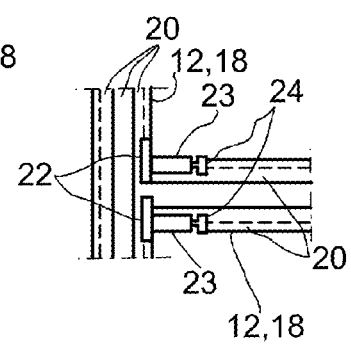

SYSTEM FOR PROTECTING STORED GOODS

This application is a National Stage application of International Application No. PCT/EP2012/062351, filed Jun. 26, 2012, which claims the benefit of U.S. Provisional Application No. 61/501,318, filed Jun. 27, 2011, the entire contents of which are hereby incorporated herein by reference.

The invention relates to a system for protecting stored goods in storage rooms from pests and to a method for protecting stored goods in a storage room from pests by applying the system.

Many food, tobacco and other products of natural origin need to be transported over long distances, or have to be stored for a considerable amount of time, e.g. as part of a ripening process, before they are delivered to retailers and consumers. During this time these products are prone to infestation by various pests. E.g., every year, tobacco at a cost of 400 million US dollars is lost to pest infestation. Over 500 million US dollars in stored cocoa and coffee—4% and 5%, respectively—is also lost to pests on an annual basis.

Accordingly, it is a continuous challenge to minimize losses of food and other products to pests during transport and storage.

Currently mainly fumigation, heating and freezing procedures are used to control pests in warehouses. However, every fumigation requires sealing of the storage facility or a section of the warehouse. In addition, most fumigants are highly toxic for humans. Thus, if not properly handled, they pose a potential health hazard for the workers engaged. In addition, residues of the fumigant in the stored products must be avoided.

Alternatives to the presently practiced methods are, therefore, highly desirable.

WO 2007/144401 discloses a method for protecting tobacco from harmful organisms during storage by covering the tobacco with a net that has a protective activity against the harmful organism.

WO 2008/052913 discloses a method for protecting crop plants from harmful organisms, comprising the step of covering one or more of the plants with a device, comprising a stabilizing structure and a meshed fabric, where the meshed fabric is impregnated with a pesticide and is penetrable by light, air and water.

However, neither of these documents is directed to the specific needs of protecting goods in warehouses of modern global transport and logistics. In order to be feasible in such an environment a system for protecting goods must fulfill various requirements such as:
  avoidance of health hazards to the workers, and pesticide residues in the stored goods,
  flexibility to adapt the system to different types of warehouses worldwide,
  minimal use of warehouse flooring space,
  ability to withstand corrosive environments,
  ease of installation and use,
  physical stability,
  ease and safety of handling in operation.

It has now been found that the above requirements can be met by a system for protecting stored goods in a storage room, comprising one or more storage constructions formed by pesticide treated nets, capable of enclosing the stored goods.

Accordingly, in one aspect of the invention a system for protecting stored goods in a storage room, comprising one or more storage constructions formed by pesticide treated nets, capable of enclosing the stored goods,
and wherein the storage construction comprises further a support frame, means for suspending the support frame, means for opening and closing the storage construction on at least one section in a suspended state,
and means for avoiding an overall structural collapse if a net gets entangled.

In a further aspect of the invention there is provided a method for protecting stored goods in a storage room, comprising the steps of installing a system according to the invention in the storage room and placing the goods inside the storage construction.

The system of the invention provides several advantages such as
  avoidance of health hazards to the workers, and pesticide residues in the stored goods,
  flexibility to adapt the system to different types of warehouses worldwide,
  minimal use of warehouse flooring space,
  ability to withstand corrosive environments,
  ease of installation and use,
  physical stability,
  ease and safety of handling in operation.

The system can be adapted to storage rooms of any size from a small storage room to an industrial size warehouse by changing the size and number of the storage constructions. Depending on the storage room, the system encloses the sides and top or either the sides or the top of the stored goods.

Pests must not be allowed to enter the protected storage constructing. To achieve a tight sealing the nets are pooling at the base of the storage constructions. To ensure that no gap is formed at the base it is preferred for the nets to include a weighted rope.

The adaptability of the system is achieved by providing a support frame wherein the support frame comprises one or more sections wherein each section of the support frame is either a rigid or a flexible element, e.g. rigid beams, ropes, cables and/or chains and wherein each section provides means to fasten the pesticide treated nets comprising guide ropes, clamps, slots, bolts, hooks and/or rollers, and wherein the support frame further comprises joining elements to join the sections of the frame and connecting elements to connect the frame to the means for suspending the support frame.

The support frame can be adapted to any shape required to protect the stored goods and can easily span large distances using rigid beams or strong cables. Rigid frames allow the use of rounded shapes and give the system stability against unwanted movements of the net. Flexible frames are lighter and allow the installation of the system in situation with little available space or where the larger weight of a rigid frame cannot be supported.

For the spanning of large distances, two or more support frames can be stacked such that their strength is increased.

In a preferred embodiment of the invention, the support frame is made of rigid beams, wherein the rigid beams are extruded section parts. Especially preferred are extruded section parts made of aluminum.

In this preferred embodiment, the joining elements to join the different sections of the frame and the connection elements to connect the support frame to the suspending means comprise slots in the extrusion parts, nuts and bolts.

The sections of the frame can also be welded together, if the chosen configuration of the support frame is not intended to be changed or to be adapted to different storage situations.

The support frame of the system is mounted by either

A) fixing the support frame at the ceiling of the storage room using suspending means which comprise mounting elements to affix the suspending means to the ceiling and/or support structure of the storage room and connecting elements to connect the support frame to the mounting elements, wherein the mounting elements comprise clamps, brackets and/or bolts, or B) fixing the support frame on at least two walls of the storage room using suspending means which comprise mounting elements to affix the suspending means to the walls and connecting elements to connect the support frame to the mounting elements, wherein the mounting elements comprise clamps, brackets and/or bolts, or C) fixing the support frame on a stand which is placed and/or fixed on the floor of the storage room, wherein the stand is comprising rigid beams and connecting elements to receive the support frame, wherein the connecting elements comprise rigid beams, ropes, cables, chains and/or pulleys, wherein the ropes, cables and/or chains are provided with tensioning elements and wherein the connecting elements are fixed to the support frame using fastening elements.

At the initial installation of the system the pesticide treated nets can be mounted to the support frame while the support frame is on the ground or after the support frame has been suspended. After the initial installation of the system it is preferred to exchange the nets while the support frame remains in a suspended state so that stored goods need not to be removed from the storage construction.

Suitable fastening elements are known to the expert and include for example bolts, screws, nuts, clamps and brackets.

If the suspending means are to be mounted to the ceiling of the storage room, it is preferred to fix the suspending means to the support structure of the building. Clamps are preferred as mounting means to affix the suspending means in the case of circular or I beams, while bolts are the preferred mounting means in the case of a concrete structure.

As it is desirable to assemble the support frame on the floor, suspending means wherein the connecting elements comprise pulleys, and are arranged so that the height of the support frame can be adjusted, are preferred.

In a case when the support frame is suspended by a stand, the use of a stand comprising hinges is preferred. The hinges on the stand are arranged such that the beams with the connecting elements to receive the support frame can be folded. In the folded state the stand can be easily transported to the site of installation. Further, the folding mechanism can function as a lifting mechanism if combined with ropes/cables/chains and/or pulleys. This allows the support frame to be assembled on the floor of the warehouse.

In a further embodiment the stand comprises means to move the stand. These means can, for example, comprise wheels and a break to allow easy movement and safe placement of the stand.

In another embodiment of the invention the stand comprises inflatable elements. This reduces the weight of the stand and allows a quick installation by inflating the stand using compressed air.

In a preferred embodiment the stand comprises mounting means to mount the stand to the base of the warehouse. This embodiment is especially preferred if the height of the stand is greater than or about the same as the width and/or the length of the storage construction. The mounting means comprise clamps, brackets, screws and/or bolts. If the combined weight of the support stand, the support frame and the nets is larger than the maximum allowed load of the warehouses basis it is preferred to use a separate base for the support stand.

If the support frame must bridge large distances between connections of the support frame to the suspending means, cross-beams and/or additional cables/ropes/chains can be inserted into the construction to improve the strength. The cross-beams can also be used to increase the rigidity of the construction to restrict unwanted motion of the storage construction. The same applies to the suspending means. Strength and rigidity of the suspending means can be improved by the incorporation of cross beams and/or cables/ropes/chains.

The incorporation of additional cross beams and/or cables/ropes/chains in the suspending means is especially preferred if the warehouse's structure does only allow for the fixing of the suspending means at certain locations.

Additional cross beams and/or cables/ropes/chains can also be included into the support frame to receive the strain caused by the nets.

One important aspect of the invention is the ease of use of the system in the daily routine of a warehouse. The system must allow for easy placement and removal of the protected goods. This is achieved by providing the storage construction with at least one section which can be opened by lifting the net or drawing the net aside.

The support frame can be provided with means to manually open/close the at least one section of the net. These means comprise cables/ropes/chains and pulleys. The manual operation of the storage construction can interfere with the daily operation of a large industrial size warehouse as a driver of a fork lift must dismount to operate the net.

In order not to interfere with the warehouse routine, it is preferred that the at least one section of the net can be opened and closed quickly, preferably in less than a minute, by an automated mechanism. This is achieved by providing the support framework with a motor and means to control the motor.

In one embodiment of the invention, at least one section of the support frame is provided with ropes that extend from the support frame to the bottom of the net and the ropes are arranged such that they can be pulled by the motor. The net can then be lifted and lowered by activating the motor.

In another embodiment of the invention the ropes are suspended from the support frame and form straps which hold the net. The net can then be lifted by pulling on one end of the ropes, thus decreasing the size of the strap.

In a preferred embodiment of the invention, the net to be lifted further comprises a pooling beam. This allows the net to be lifted uniformly over the entire length of the section and reduces undesired movements of the net.

If a single three dimensional net is used to form the storage construction it is preferred that the sewing pattern of the net includes additional net material at or near the seams between the side to be opened by the means to open the storage construction and the two adjacent sides. This allows the net to form a clear opening of approximately rectangular shape.

In another embodiment of the invention, the net on at least one section of the support frame is mounted using rollers and the rollers are arranged such that they can be moved by the motor to draw the net.

It is preferred that a driver of a forklift is not required to dismount in order to operate the net. This is achieved by providing means to control the motor in the form of a wired remote, a radio frequency (RF) or infra-red (IR) wireless remote or a motion sensor.

A wired remote can be arranged by hanging from the ceiling or mounting to a stand such that a fork lift driver can operate the remote from inside the forklift. Wireless remotes can be operated from any location near the storage construction, including from the inside of a forklift. In the case of wireless remotes, it is preferred to equip each used forklift or each staff member with these remotes.

If the system for the protection of stored goods comprises more than one storage construction it is preferred to assign a unique code to each storage construction. An operator can then select the storage construction to be opened or closed by transmitting the corresponding code using the wireless remote.

In a further embodiment of the invention each storage construction is provided with an IR detector for detecting signals sent by the remote and the IR detector of each storage construction is arranged such that the storage construction to be opened is selected by pointing the IR wireless remote in the direction of the storage construction. This eliminates the need to remember or record different codes, thus allowing for an easy and intuitive selection of the net to be operated.

Further it is an important aspect of the invention to provide a system that is easy and safe to use. In the daily warehouse routine forklifts are used. These devices possess great strength and pose a potential threat to the hanging nets. The forklift might drive over the pooling parts of the net or the net could get entangled in the forks of the forklift. In both cases great forces are exerted onto the net and the structures suspending the net. These forces could tear the net making it unusable. The forces can even lead to a complete collapse of the storage construction if the forces exceed the maximum load capacity of the support frame or suspending means.

It is therefore an important aspect of the invention to provide means for avoiding an overall structural collapse. These means are used to fix the net to the support frame such that the fixture is released if the pull on the net exceeds a certain maximum load. These means can be one or more of Velcro strips, compression clamp strips, holding clamps, bolts or hooks provided with breaking points.

One important aspect of the invention is to reduce the amount of pesticides required to control the pest levels, especially to avoid fumigation of the warehouse. This is achieved by effectively hindering insects and pests to enter the protected storage space inside the system. Thus it is of great importance, that the warehouse and the stored goods are initially pest free.

To achieve the required initial pest levels, fumigation of the warehouse might still be necessary. It is therefore preferred to choose the materials used in the construction of the system to be able to withstand corrosive environments, thus allowing fumigation of the warehouse with the system in place.

Further it is important to monitor the pest levels in the warehouse and inside the storage constructions in order to assess the effectiveness of the system.

Thus in a preferred embodiment of the system the system further comprises means to monitor pest infections. In a preferred embodiment these means comprise pheromone traps arranged in the protected area near the stored goods and/or outside the storage constructions.

In a further aspect of the invention there is provided a method for installing the system for protecting stored goods in a storage room, comprising the steps of assembling the support frame at the site of installation, installing of the means to suspend the support frame at the site of installation, and connecting the support frame to the means to suspend the support frame, lifting the support frame and mounting the net to the support frame.

In one embodiment of the invention the required parts for the support frame and/or the means for suspending the support frame are delivered in kit-form and are assembled at the site of installation. The kits save room during storage and transport and can be easily delivered. At the site of installation only little space is required. The support frame can be assembled around the stored goods. The means for suspending the support frame can be fixed to the ceiling and/or walls using ladders or lifts or a support stand can be erected on the ground. After fixing the support frame to the means for suspension, the support frame and the attached nets are lifted to the desired height.

In one embodiment of the invention the nets are attached to the support frame while the frame is located on the floor and the support frame can be lowered again to the floor if the nets need to be exchanged.

In a preferred embodiment of the invention the nets are mounted to the support frame while the support frame is in a suspended state. If an exchange of a net is necessary, it is preferred to perform the exchange while the support frame remains in a suspended state. The nets should be exchanged in case of declining efficacy of the treated nets or damages to the nets.

When a net is mounted to the support frame while the support frame is in a suspended state, it is preferred to first attach the net to the frame using means which allow the net to be moved. Suitable means include rollers, hooks and/or straps. After the net is completely suspended from the support frame and moved into the correct position the net is attached to the support frame using means which allow the net to be tightened. Suitable means to attach the net in a tightened state to the support frame comprise compression clamp strips, Velcro strips and/or holding clamps.

In another embodiment of the invention the support frame and/or the means for suspending the support frame are in part or completely preassembled in the factory.

In a further aspect of the invention there is provided a method for protecting stored goods in a storage room, comprising the steps of installing a system according to the invention in the storage room and placing the goods inside the storage construction.

In a preferred embodiment of the invention, the net on at least one section of the support frame is provided with means for opening and closing the storage construction and the storage construction is opened before moving/removing goods into or out of the storage construction and closed afterwards.

The storage constructions should remain closed at all times and the net should only be opened to place goods into or to remove goods out of the storage construction. Thus a preferred embodiment of the invention further comprises a motion sensor and an opened section of the storage construction is automatically closed if the motion sensor does not detect any motion during a predetermined time span.

In a preferred embodiment of the invention, the goods are treated against pests before placing the goods inside the storage construction. The treatment against pests can comprise fumigation.

In another preferred embodiment the pest levels inside the storage constructions and/or the warehouse are monitored. The levels are tracked over time such that the efficacy of the system against pests can be assessed. If the pest levels rise and/or after the nets have been in use for a certain predetermined amount of time the pesticide treated nets should be replaced.

In one embodiment of the invention the exchange of nets comprises the steps of lowering the support frame to the floor, removing the used net, attaching the new net to the support frame and lifting the support frame to the desired height of the storage construction.

In a preferred embodiment of the invention the support frame remains in a suspended state during the net exchange procedure.

It is preferred that used nets are returned to the manufacturer for disposal.

The nets employed according to the invention are impregnated with one or more pesticides. In general, the pesticide is incorporated into the material (e.g. into the plastics matrix) or applied to the surface of the material or both.

In a preferred embodiment, the material is treated with a composition comprising:
a) at least one pesticide (component A), and
b) at least one polymeric binder (component B).

Such compositions are disclosed, e.g., in WO 2007/144401.

The term "pesticide" as used herein comprises insecticides, repellents and fungicides.

The term "insecticides" as used herein comprises agents with arthropodicidal (specifically, insecticidal, acaricidal and miticidal), molluscicidal and rodenticidal activity, if not otherwise stated in the context.

The term "fungicides" as used herein comprises agents with fungicidal, microbicidal and viricidal activity, if not otherwise stated in the context.

Preferably, the pesticide is an insecticide or repellent.
Pesticide (Component A)

Preferably, the pesticide is an insecticide and/or repellent with a fast paralyzing or killing effect of the insect and low mammalian toxicity. Suitable insecticides and/or repellents are known by a person skilled in the art. Suitable insecticides and repellents are disclosed e.g. in E. C. Tomlin et al., The Pesticide Manual, 13ed., The British Crop Protection Council, Farnham 2003, and the literature cited therein.

Preferred insecticides and/or repellents are mentioned below:
pyrethroid compounds such as
Etofenprox: 2-(4-ethoxyphenyl)-2-methylpropyl-3-phenoxybenzyl ether,
Chlorfenapyr: 4-bromo-2-(4-chlorophenyl)-1-ethoxymethyl-5-(trifluoromethyl)pyrrole-3-carbonitrile,
Fenvalerate: (RS)-alpha-cyano-3-phenoxybenzyl (RS)-2-(4-chlorophenyl)-3 methylbutyrate,
Esfenvalerate: (S)-alpha-cyano-3-phenoxybenzyl(S)-2-(4-chlorophenyl)-3-methylbutyrate,
Fenpropathrin: (RS)-alpha-cyano-3-phenoxybenzyl 2,2,3,3-tetramethylcyclopropanecarboxylate,
Cypermethrin: (RS)-alpha-cyano-3-phenoxybenzyl (1RS)-cis, trans-3-(2,2-dichlorovinyl)-2,2-dimethylcyclopropanecarboxylate,
alpha-Cypermethrin: racemate comprising the (S)-α-(1R) and (R)-α-(1S)diastereomers,
Permethrin: 3-phenoxybenzyl (1RS)-cis, trans-3-(2,2-dichlorovinyl)-2,2-dimethylcyclopropanecarboxylate,
Cyhalothrin: (RS)-alpha-cyano-3-phenoxybenzyl(Z)-(1RS)-cis-3-(2-chloro-3,3,3-trifluoroprop-1-enyl)-2,2-dimethyl-cyclopropanecarboxylate, lambda-cyhalothrin,
Deltamethrin: (S)-alpha-cyano-3-phenoxybenzyl (1R)-cis-3-(2,2-dibromovinyl)-2,2-dimethylcyclopropanecarboxylate,
Cycloprothrin: (RS)-alpha-cyano-3-phenoxybenzyl (RS)-2, 2-dichloro-1-(4-ethoxyphenyl)cyclopropanecarboxylate,
Fluvalinate: alpha-cyano-3-phenoxybenzyl N-(2-chloro-alpha, alpha, alpha, alpha-trifluoro-p-tolyl)-D-valinate,
Bifenthrin: (2-methylbiphenyl-3-ylmethyl)0(Z)-(1RS)-cis-3-(2-chloro-3,3,3-trifluoro-1-propenyl)-2,2-dimethylcyclopropanecarboxylate,
2-methyl-2-(4-bromodifluoromethoxyphenyl)propyl (3-phenoxybenzyl)ether,
Tralomethrin: (S)-alpha-cyano-3-phenoxybenzyl (1R-cis)3 ((1'RS)(1',2',2',2'-tetrabromoethyl))-2,2-dimethylcyclopropanecarboxylate,
Silafluofen: 4-ethoxyphenyl(3-(4-fluoro-3-phenoxyphenyl) propyl}dimethylsilane,
D-fenothrin: 3-phenoxybenzyl (1R)-cis, trans-chrysanthemate,
Cyphenothrin: (RS)-alpha-cyano-3-phenoxybenzyl (1R-cis, trans)-chrysanthemate, D-resmethrin: 5-benzyl-3-furylmethyl (1R-cis, trans)-chrysanthemate,
Acrinathrin: (S)-alpha-cyano-3-phenoxybenzyl (1R-cis(Z))-(2,2-dimethyl-3-(oxo-3-(1,1,1,3,3,3-hexafluoropropyloxy)propenyl(cyclopropanecarboxylate,
Cyfluthrin: (RS)-alpha-cyano-4-fluoro-3-phenoxybenzyl 3-(2,2-dichlorovinyl)-2,2-dimethylcyclopropanecarboxylate,
Tefluthrin: 2,3,5,6-tetrafluoro-4-methylbenzyl (1RS-cis(Z))-3-(2-chloro-3,3,3-trifluoroprop-1-enyl)-2,2-dimethylcyclopropanecarboxylate,
Transfluthrin: 2,3,5,6-tetrafluorobenzyl (1R-trans)-3-(2,2-dichlorovinyl)-2,2-dimethylcyclopropanecarboxylate,
Tetramethrin: 3,4,5,6-tetrahydrophthalimidomethyl (1RS)-cis, trans-chrysanthemate,
Allethrin: (RS)-3-allyl-2-methyl-4-oxocyclopent-2-enyl (1RS)-cis, trans-chrysanthemate,
Prallethrin: (S)-2-methyl-4-oxo-3-(2-propynyl)cyclopent-2-enyl (1R)-cis, trans-chrysanthemate,
Empenthrin: (RS)-1-ethynyl-2-methyl-2-pentenyl (1R)-cis, trans-chrysanthemate,
Imiprothrin: 2,5-dioxo-3-(prop-2-ynyl)imidazolidin-1-ylmethyl (1R)-cis, trans-2,2-dimethyl-3-(2-methyl-1-propenyl)-cyclopropanecarboxylate,
D-flamethrin: 5-(2-propynyl)-furfuryl (1R)-cis, trans-chrysanthemate, and 5-(2-propynyl)furfuryl 2,2,3,3-tetramethylcyclopropanecarboxylate;
Pyriproxyfen: 4-phenoxyphenyl (RS)-2-(2-pyridyloxy)propyl ether; pyrethrum;
d-d, trans-cyphenothrin: (RS)-α-cyano-3-phenoxybenzyl (1RS,3RS;1RS,3SR)-2,2-dimethyl-3-(2-methylprop-1-enyl)cyclopropanecarboxylate;
Lambda-cyhalothrine:
α-cyano-3-phenoxybenzyl-3-(2-chloro-3,3,3-trifluoroprop-1-enyl)-2,2-dimethylcyclopropane carboxylate, as a 1:1 mixture of (Z)-(1R,3R), R-ester and (Z)-(1S,3S), S-ester.
Carbamate compounds such as
Alanycarb: S-methyl-N[[N-methyl-N-[N-benzyl-N(2-ethoxy-carbonylethyl)aminothio]carbamoyl]thioacetimidate,
Bendiocarb: 2,2-dimethyl-1,3-benzodioxol-4-yl-methylcarbamate),
Carbaryl(1-naphthyl N-methylcarbamate,
Isoprocarb: 2-(1-methylethyl)phenyl methylcarbamate,
Carbosulfan: 2,3 dihydro-2,2-dimethyl-7-benzofuranyl [(dibutylamino)thio]methylcarbamate,
Fenoxycarb: Ethyl[2-(4-phenoxyphenoxy)ethyl]carbamate, Indoxacarb: Methyl-7-chloro-22,3,4°,5-tetrahydro-2-[methoxycarbonyl(-4-trifluoromethoxyphenyl)]
Propoxur: 2-isopropyloxyphenol methylcarbamate,
Pirimicarb: 2-dimethylamino-5,6-dimethyl-4-pyrimidinyl-dimethylcarbamate,
Thiodiocarb: Dimethyl N,N'(thiobis((methylimino)carbonoyloxy)bisethanimidiothioate).
Methomyl: S-methyl N-((methylcarbamoyl)oxy)thioacetamidate,
Ethiofencarb: 2-((ethylthio)methyl)phenyl methylcarbamate,
Fenothiocarb: S-(4-phenoxybutyl)-N,N-dimethyl thiocarbamate,
Cartap: S,S'-(2-5 dimethylamino)trimethylene)bis(thiocarbamate)hydrochloride,
Fenobucarb: 2-sec-butylphenylmethyl carbamate,
XMC: 3,5-dimethylphenyl-methyl carbamate,
Xylylcarb: 3,4-dimethylphenylmethylcarbamate;
organophosphorous compounds such as
Trichlorfon: Phosphoric acid, (2,2,2-trichloro-1-hydroxyethyl)-, dimethyl ester
Fenitrothion: O,O-dimethyl O-(4-nitro-m-tolyl)phosphorothioate,
Diazinon: O,O-diethyl-O-(2-isopropyl-6-methyl-4-pyrimidinyl)phosphorothioate,
Pyridaphenthion: O-(1,6-dihydro-6-oxo-1-phenylpyrazidin-3-yl) O,O-diethyl phosphorothioate,
Pirimiphos-Etyl: O,O-diethyl O-(2-(diethylamino)6-methyl-pyrimidinyl)phosphorothioate,
Pirimiphos-Methyl: O-[2-(diethylamino)-6-methyl-4 pyrimidinyl]O,O-dimethyl phosphorothioate,
Etrimphos: O-6-ethoxy-2-ethyl-pyrimidin-4-yl-O,O-dimethyl-phosphorothioate,
Fenthion: O,O-dimethyl-O-[-3-methyl-4-(methylthio)phenyl phosphorothioate,
Phoxim: 2-(diethoxyphosphinothoyloxyimino)-2-phenylacetonitrile,
Chlorpyrifos: O,O-diethyl-O-(3,5,6-trichloro-2-pyrinyl) phosphorothioate,
Chlorpyriphosmethyl: O,O-dimethyl O-(3,5,6-trichloro-2-pyridinyl)phosphorothioate,
Cyanophos: O,O-dimethyl O-(4 cyanophenyl)phosphorothioate,
Pyraclofos: (R,S)[4-chlorophenyl)-pyrazol-4-yl]-O-ethyl-S-n-propyl phosphorothioate,
Acephate: O, S-dimethyl acetylphosphoroamidothioate,
Azamethiphos: S-(6-chloro-2,3-dihydro-oxo-1,3-oxazolo[4,5-b]pyridine-3-ylmethyl phosphorothioate,
Malathion: O,O-dimethyl phosphorodithioate ester of diethyl mercaptosuccinate,
Temephos: (O,O'(thiodi-4-1-phenylene) O,O,O,O-tetramethyl phosphorodithioate,
Dimethoate: ((O,O-dimethyl S-(n-methylcarbamoylethyl) phosphorodithioate,
Formothion: S[2-formylmethylamino]-2-oxoethyl]-O,O-dimethyl phosphorodithioate,
Phenthoate: O,O-dimethyl S-(alpha-ethoxycarbonylbenzal)-phosphorodithioate;
Iodofenphos: O-(2,5-dichloro-4-iodophenyl)-O,O-dimethyl-phosphorthioate.
Insecticides with a sterilising effect on adult mosquitoes such as
1-(alfa-(chloro-alpha-cyclopropylbenzylidenamino-oxy)-p-tolyl)-3-(2,6-difluorobenzoyl)urea,
Diflubenzuron: N-(((3,5-dichloro-4-(1,1,2,2-tetrafluoroethoxy)phenylamino)carbonyl)2,6 difluoro benzamid,
Triflumuron: 2-Chloro-N-(((4-(trifluoromethoxy)phenyl)-amino-)carbonyl)benzamide, or a triazin such as N-cyclopropyl-1,3,5-triazine-2,4,6-triamin; and The repellent is preferably selected from N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1, 3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), Cymopogan nartdus (citronella), IR3535 (ethyl butylacetylaminopropionate), icaridin (1-piperidinecarboxylic acid 2-(2-hydroxyethyl)-1-methylpropylester).

Suitable fungicides are for example
Azoles such as Bitertanol, Bromoconazole, Cyproconazole, Difenoconazole, Dinitroconazole, Epoxiconazole, Fenbuconazole, Fluquiconazole, Flusilazole, Flutriafol, Hexaconazole, Imazalil, Ipconazole, Metconazole, Myclobutanil, Penconazole, Propiconazole, Prochloraz, Prothioconazole, Simeconazole, Tebuconazole Tetraconazol, Triadimefon, Triadimenol, Triflumizol, Triticonazol;
Strobilurines such as Azoxystrobin, Dimoxystrobin, Fluoxastrobin, Kresoxim-methyl, Metominostrobin, Orysastrobin, Picoxystrobin, Pyraclostrobin and Trifloxystrobin;
Acylalanines such as Benalaxyl, Metalaxyl, Mefenoxam, Ofurace, Oxadixyl;
Aminderivatives such as Aldimorph, Dodine, Dodemorph, Fenpropimorph, Fenpropidin, Guazatine, Iminoctadine, Spiroxamin, Tridemorph;
Anilinopyrimidines such as Pyrimethanil, Mepanipyrim, Cyprodinil;
Dicarboximide such as Iprodion, Myclozolin, Procymidon, Vinclozolin;
Cinnamic amides and derivatives such as Dimethomorph, Flumetover, Flumorph;
Antibiotics as Cycloheximide, Griseofulvin, Kasugamycin, Natamycin, Polyoxin, Streptomycine;
Dithiocarbamates such as Ferbam, Nabam, Maneb, Mancozeb, Metam, Metiram, Propineb, Polycarbamat, Thiram, Ziram Zineb;
Heterocyclic compounds such as Anilazin, Benomyl, Boscalid, Carbendazim, Carboxin, Oxycarboxin, Cyazofamid, Dazomet, Dithianon, Famoxadon, Fenamidon, Fenarimol, Fuberidazol, Flutolanil, Furametpyr, Isoprothiolan, Mepronil, Nuarimol, Picobenzamid, Probenazol, Proquinazid, Pyrifenox, Pyroquilon, Quinoxyfen, Silthiofam, Thiabendazol, Thifluzamid, Thiophanat-methyl, Tiadinil, Tricyclazol, Triforine M Anorganika;
Nitrophenylderivatives such as Binapacryl, Dinocap, Dinobuton, Nitrophthal-isopropyl;
Phenylpyrroles such as Fenpiclonil, Fludioxonil;
Derivatives of sulfenic acid such as Captafol, Captan, Dichlofluanid, Folpet, Tolylfluanid;
Other fungicides such as Acibenzolar-S-methyl, Benthiavalicarb, Carpropamid, Chlorothalonil, Cyflufenamid, Cymoxanil, Dazomet, Diclomezin, Diclocymet, Diclofluanid, Diethofencarb, Edifenphos, Ethaboxam, Fenhexamid, Fentin-Acetat, Fenoxanil, Ferimzone, Fluazinam, Fosetyl, Fosetyl-Aluminium, Phosphoric Acid, Iprovalicarb, Hexachlorbenzene, Metrafenon, Pencycuron, Propamocarb, Phthalid, Toloclofos-methyl, Quintozene, Zoxamid.

Preferred insecticides and/or repellents of the pesticidal composition of the invention may be either one or a mixture. Preferred mixtures of pesticides are mixtures of insecticides and/or repellents with similar diffusion/migration properties. This group of insecticides and/or repellents may include synthetic pyrethroids such as alphacypermethrin, cyfluthrin, deltamethrin, etofenprox and permethrin, other pyrethroids such as bifenthrine, and non-pyrethroids such as chlorfenapyr.

Finishing

The term "finishing" means according to the invention any type of treatment of the net with the insecticide mixture, by means of which treatment a homogeneous distribution of the mixture on or in the net is achieved. In this context, homogeneous means that the concentration of a certain insecticide is essentially the same at any point of the areas.

In one embodiment, finishing is effected by coating the net or, preferably, monofilaments or multifilaments or fibers of which the net is produced with the insecticide mixture together with a binder (variant A).

In a further embodiment, finishing is effected by admixing the insecticide mixture to a polymer and coextruding the polymer and the insecticide mixture to give a monofilament which is processed to give the net according to the invention (variant B).

Finishing by Coating with an Insecticide-Mixture-Comprising Binder (Variant A)

The function of the binder is to fix the insecticide mixture on the monofilaments or multifilaments or fibers of which the net is produced, or on the finished net ("end of line coating") (hereinbelow described with reference to a net). The result achieved hereby is that the active compound cannot be leached, or at least only very slowly.

The polymeric binder may, in principle, take the form of any binder with the proviso that the binders are capable of fixing the insecticide mixture in particular to textile materials. Binders which are therefore preferred are those known from the field of textile finishing and textile coating. Naturally, it is also possible to employ a mixture of a plurality of different binders.

Examples comprise homo- or copolymers comprising (meth)acrylates, or polyurethanes, polyisocyanurates or waxes, such as polyethylene waxes.

For example, they may be binders which can be obtained by polymerization of ethylenically unsaturated monomers, preferably at least one monomer selected from the group consisting of (meth)acrylates, in particular $C_1$- to $C_{12}$-esters of (meth)acrylic acid, (meth)acrylates having crosslinking groups, (meth)acrylic acid, maleic acid or maleic esters, acrylonitrile, styrene, vinyl acetate, vinyl alcohol, ethylene, propylene, allyl alcohol or vinyl chloride.

In a preferred embodiment of the invention, this is a copolymer of ethylenically unsaturated monomers which comprises, as monomers, 50 to 95% by weight of at least one (meth)acrylate (A) of the general formula $H_2C=CHR^1-COOR^2$, where $R^1$ is H or methyl and $R^2$ is an aliphatic, linear or branched hydrocarbon radical having 1 to 12 carbon atoms, preferably 2 to 10 carbon atoms. $R^1$ is preferably H. Examples of suitable radicals $R^2$ comprise in particular methyl, ethyl, n-butyl or 2-ethylhexyl radicals, preferably ethyl, n-butyl or 2-ethylhexyl radicals. Moreover, the copolymer comprises 1 to 20% by weight of (meth)acrylic acid or (meth)acrylic acid derivatives (B) with additional functional groups. This may take the form in particular of a (meth)acrylic ester and/or (meth)acrylamides. The functional groups serve to bind the binder to the nets and can furthermore be used for crosslinking. For example, they may take the form of ω-hydroxyalkyl(meth)acrylic esters, (meth)acrylic esters having epoxy groups such as, for example, glycidyl esters, (meth)acrylamides or derivatives thereof such as, for example, (meth)acrylic acid methylolamide of the formula $H_2C=CH(CH_3)-CO-HN-CH_2-OH$. It is at the same time possible to employ further ethylenically unsaturated, preferably monoethylenically unsaturated, monomers (C) which differ from A and B, for example acrylonitrile or styrene. As a rule, the amount of further monomers is from 0 to 30% by weight. Especially preferred is a binder which comprises 70 to 90% by weight of an acrylic ester of the formula $H_2C=CH_2-COOR^2$, where $R^2$ comprises 4 to 8 C atoms, and which is preferably n-butyl and/or 2-ethylhexyl, and furthermore 10 to 20% by weight of acrylonitrile, 1 to 10% by weight of (meth)acrylic acid or a (meth)acrylic acid derivative which has functional groups, in particular (meth)acrylic acid methylolamide.

The abovementioned preferred binders can preferably be prepared by methods known to the skilled worker, preferably by means of emulsion polymerization. Preferably an acrylate binder, in particular a copolymer, can be obtained by emulsion polymerization of the components B1 to B4, and optionally B5.

As component B1, one or more, preferably 1, 2 or 3, especially preferably 1, (meth)acrylate(s) of the formula (I)

$$H_2C=CR^1-COOR^2 \quad (I)$$

is/are employed, where the symbols have the following meanings:

$R^1$ is H or $CH_3$, preferably H, and $R^2$ is $C_1$-$C_{10}$-alkyl, preferably methyl, ethyl, n-propyl, i-propyl, n-butyl, i-butyl, sec-butyl, t-butyl, n-pentyl, sec-pentyl, neopentyl, 1,2-dimethylpropyl, i-amyl, n-hexyl, i-hexyl, n-heptyl, n-octyl, 2-ethylhexyl, n-nonyl or n-decyl, especially preferably methyl, ethyl, n-butyl or 2-ethylhexyl, very especially preferred are ethyl, n-butyl or 2-ethylhexyl.

Preferred as component B1 are methyl acrylate, ethyl acrylate, n-butyl acrylate, 2-ethylhexyl acrylate and methyl methacrylate. Also preferred are butyl acrylate on its own or in admixture with methyl methacrylate or ethyl acrylate. Especially preferred is n-butyl acrylate.

Substances which are employed as component B2 are at least one monomer from the group consisting of N-methylolacrylamide, N-methylolmethacrylamide, N,N'-bismethylolmaleic diamide and N,N'-bismethylolfumaric diamide.

Preferred are N-methylolacrylamide and N-methylolmethacrylamide, in particular N-methylolmethacrylamide.

Substances which are employed as component B3 are one or more monomers, preferably one or two monomers, selected from the group consisting of acrylic acid, methacrylic acid, vinylsulfonic acid, maleic acid and fumaric acid. Preferred are acrylic acid and methacrylic acid; acrylic acid is especially preferred.

Substances which are employed as component B4 are one or more monomers, preferably one or two monomers, selected from groups B4A and/or B4B.

Monomers of group B4A are those of the formula (II) and/or (III)

$$H_2C=CR^3X \quad (II)$$

$$ZHC=CHZ \quad (III)$$

where the symbols have the following meanings:

$R^3$ is H or $CH_3$, preferably H;

X is Z, $-CO-NH-CH_2-NH-CO-CR^3=CH_2$ or $COO-CH_2-CO-CH_2-COOR^4$, preferably Z;

Z equals $CONH_2$, $CONH-CH_2-OR^5$, $COO-Y-OH$, COO-glycidyl, CHO, $CO-Y-OH$, preferably $CONH_2$;
Y is $C_1$-$C_8$-alkylene, preferably $C_2$-$C_6$-alkylene, and
$R^4$, $R^5$ are identical or different and are a linear or branched $C_1$-$C_{10}$-alkyl group; and (meth)acrylic-modified benzophenones, as described, for example, in EP-A 0 346 734.

Preferred as monomers from group B4A are acetoacetyl acrylate, acetoacetyl methacrylate, acrylamide, methacrylamide, maleic diamide, N-methoxymethylacrylamide, N-n-butoxymethylacrylamide, 3-hydroxypropyl acrylate, 3-hydroxypropyl methacrylate, 4-hydroxybutyl acrylate, 4-hydroxybutyl methacrylate, 6-hydroxyhexyl acrylate, 6-hydroxyhexyl methacrylate, 2-hydroxy-3-chloropropyl acrylate, 3-hydroxy-3-chloropropyl methacrylate, glycidyl acrylate and glycidyl methacrylate. Especially preferred are acrylamide, 3-hydroxypropyl methacrylate, butanediol monoacrylate acetylacetate, glycidyl methacrylate, and 4-acryloxybenzophenone.

Substances which are employed as monomers from group B4B are allyl acrylate, methallyl acrylate, allyl methacrylate, methallyl methacrylate, diallyl maleate, dimethylallyl maleate, allyl fumarate, methallyl fumarate, diallyl phthalate, dimethylallyl phthalate, diallyl terephthalate, dimethallyl terephthalate, p-divinylbenzene, butane-1,4-diol diallyl ether and butane-1,4-diol dimethylallyl ether.

Preferred monomers of group B4 are those of group B4A, the use of one or two monomers from among this group being preferred.

Preferred monomers of group B5 are those of group B5A, and also vinylaromatic monomers of group B5B.

It is preferred to employ acrylonitrile or methacrylonitrile, preferably acrylonitrile, as component B5A.

Preferred as component B5B are styrene and α-methylstyrene, styrene being especially preferred.

In a preferred embodiment, acrylonitrile is employed as monomer of component B5 for the preparation of the acrylate binder.

The acrylate binder (B) is obtainable by emulsion polymerization of (data in % by weight are in each case based on the total amount of B):
b1) 20 to 93% by weight, preferably 50 to 90% by weight, especially preferably 60 to 90% by weight, in particular 75 to 85% by weight, of component B1;
b2) 1 to 5% by weight, preferably 1.5 to 3% by weight of component B2;
b3) 0.2 to 5% by weight, preferably 0.5 to 4% by weight, especially preferably 0.75 to 4% by weight, in particular 1 to 3% by weight of component B3;
b4) 0 to 7% by weight, preferably 0 to 5% by weight, especially preferably 0 to 4.5% by weight, in particular 0 or 0.2 to 4.5% by weight of component B4 and
b5) 0 to 40% by weight, preferably 5 to 40% by weight, especially preferably 5 to 30% by weight, in particular 0 or 5 to 26% by weight of component B5.

Suitable processes are known to the skilled worker and described, for example, in WO 2005/064072 (page 20, line 20 to page 23, line 15).

The weight-average molecular weight of the non-crosslinked emulsion polymers obtained is generally between 40 000 and 250 000 (as determined by GPC (gel permeation chromatography)). The molecular weight is generally adjusted by using chain termination reagents, for example organosulfur compounds, in the usual amounts.

The especially preferred acrylate binder is generally obtained in the form of an aqueous dispersion and is usually employed in this form in the insecticidal formulation according to the invention.

The preferred acrylate binder can furthermore comprise usual additives known to the skilled worker, for example film formers and/or plasticizers, such as adipates, phthalates, butyl diglycol, mixtures of diesters, obtainable by reacting dicarboxylic acids with straight-chain or branched alcohols. Suitable dicarboxylic acids and alcohols are known to the skilled worker.

Others which are suitable, apart from the abovementioned binders, are silicone oils and silicone waxes, polysiloxanes, resins with fluorinated hydrocarbon radicals, melamine/formaldehyde condensates, methylolurea derivatives and curable polyesters, with silicone oils being preferred.

The preferred silicone oils and silicone waxes generally take the form of linear or cyclic polyorganosiloxanes, preferably polyalkyl- and/or polyphenylsiloxanes, alkyl being for example methyl, ethyl, propyl or octyl, preferably methyl. Particularly preferred are polydimethylsiloxanes, poly(methylphenylsiloxanes) and corresponding compounds in which a proportion of the methyl groups is replaced by higher alkyl groups. The molecular weight is preferably between 1000 and 150 000. If appropriate, the silicone oils and in particular the silicone waxes may comprise consistency regulators, for example metal soaps such as lithium stearate, highly-disperse silica, PTFE, boron nitride or urea, in order to obtain a pasty or fatty consistency.

To prepare the nets according to the invention, in particular nets, the binders may be employed in the form of a formulation in a solvent, preferably as an aqueous formulation. However, the invention also comprises the use of solvent-free formulations.

In a preferred embodiment, aqueous formulations are employed which comprise 55 to 99% by weight of water, preferably 85 to 98% by weight of water and 1 to 45% by weight, preferably 2 to 15% by weight, of solids, the quantities given being in each case based on the total of all components in the formulation. The precise concentration also depends on the adsorptivity of the textile substrate.

The solids take the form of at least one binder, the insecticidal mixture, optionally at least one crosslinker and optionally further components.

It is preferred to employ at least one water-dispersible crosslinker. In particular in the case of the preferred acrylate binder, this may preferably take the form of a crosslinker which has free isocyanate groups. These may preferably take the form of isocyanurates which have free isocyanate groups, preferably isocyanurates which are derived from aliphatic, cycloaliphatic or aromatic diisocyanates having 4 to 12 carbon atoms. Examples comprise 1,6-hexamethylene diisocyanate, 1,12-dodecane diisocyanate, 2,2'- and 2,4'-dicyclohexylmethane diisocyanate or 2,4-tolyl diisocyanate. Preferred are isocyanurates based on 1,6-hexamethylene diisocyanate. Especially preferred are isocyanurates which have additional hydrophilic groups such as, in particular, polyethylene oxide groups. The preparation of such isocyanurates is known to the skilled worker. They are preferably employed as a solution in polar aprotic solvents such as, for example, ethylene carbonate or propylene carbonate. Further details on the preferred crosslinkers having isocyanate groups are disclosed in WO 2008/052913 page 34, line 6 to page 35, line 3. It is especially preferred to employ an isocyanurate which is based on 1,6-hexamethylene diisocyanate (HMDI) and which has additional polyethylene oxide groups, the isocyanurate being dissolved in propylene carbonate (70% by weight of HMDI in propylene carbonate). The free isocyanate groups amount to approximately 11 to 12% by weight based on the solution. The crosslinker is preferably employed in an amount of from 1 to 10% by weight based on the amount of all solids of the formulation. The isocyanurate-based crosslinkers are suitable especially for crosslinking the above-named copolymers.

The formulation may furthermore comprise typical additives and adjuvants, UV stabilizers and colorants. Examples of such additives are mentioned in WO 2008/052913 page 35, line 17 to page 37, line 5.

Crosslinkers and thickeners may be employed to enable uniform coating with the treatment liquor of nets which can only be wetted with difficulty, and therefore inhomogeneously, such as, for example, polyolefin fibers. For this purpose, it would also be possible to employ water-miscible solvents, which, however, is not preferred due to the harmful effect on the environment. A person skilled in the art is familiar with the adjuvants which are conventionally used and with their concentrations.

The formulations may preferably comprise antioxidants, peroxide scavengers, UV absorbers and light stabilizers. This is particularly recommended in the case of nets which are exposed to increased UV irradiation in the open or in greenhouses. The abovementioned additives protect not only the substrate fibers, but also the active compounds, from decomposition due to radiation.

Suitable UV absorbers are described for example in WO 02/46503 or in WO 2007/077101. UV absorbers may firstly be used as a component in the formulation for finishing; secondly, they may also be incorporated as early as during the production of the fibers, for example in the case of polyolefins and polyesters. It is also possible advantageously to employ mixtures of a plurality of stabilizers which have different protective effects. As a rule, from 0.2 to 5% by weight, preferably from 0.25 to 4% and very especially preferably from 0.5 to 3.5% by weight of stabilizer is employed based on the weight of the untreated net. The amount in the formulation will be adjusted by the skilled worker to suit the task in hand.

Finishing According to Variant B by Incorporating the Insecticide Mixture into Monofilaments In a further embodiment of the invention, finishing is carried out by directly incorporating the mixture according to the invention into a monofilament which is processed for example to give fibers, of which the net according to the invention consists or which are present therein. Preferably, the net in this variant is a net.

A suitable polymer material for the monofilament into which the mixture according to the invention can be incorporated are thermo plastic polymers, preferably those based on olefinically unsaturated monomers, for example polyolefins, polyvinyl chloride, polyvinyl alcohols, poly(meth)acrylates, but also polyesters and polycarbonates, and, if appropriate, mixtures of the abovementioned polymers with each other or with thermoplastic elastomers. Especially preferred are polyethylene, for example low-density polyethylene (LDPE), such as linear low-density polyethylene (LLDPE), ultra-low density polyethylene (ULDPE), medium-density polyethylene (MDPE) and high-density polyethylene (HDPE), polyethylene resins such as copolymers of ethylene and alpha-olefins with at least three carbon atoms, polypropylene homopolymers, random copolymers and block copolymers of propylene and alpha-olefins with four and more carbon atoms, copolymers of ethylene with unsaturated carboxylic acid compounds, for example poly(ethylene/methyl methacrylate), poly(ethylene/vinyl acetate) or poly(ethylene/acrylic acid), and mixtures of such polymers and copolymers. Examples of thermoplastic elastomers comprise olefin- and styrene-based thermoplastic elastomers. Preferred are copolymers with ethylene or propylene as the main component, but also block copolymers comprising polystyrene and polyisoprene and/or polybutadiene blocks, and hydrogenated derivatives of such copolymers.

To produce the monofilaments which comprise the insecticide mixture according to the invention in a thermoplastic polymer matrix, the insecticide mixture and the polymer may be mixed by melt-kneading. It is also possible first to prepare a masterbatch by melt-kneading suitable amounts of insecticide mixture and polymer, which masterbatch is subsequently diluted to the desired concentration by melt-kneading with a further quantity of polymer. If the masterbatch method is employed, it is also possible to use different polymers for the masterbatch and for the subsequent dilution, for example an LLDPE for the masterbatch and an HDPE for diluting the masterbatch.

Besides the polymer and the insecticide mixture according to the invention, the polymer composition comprises, if appropriate, a pulverulent carrier material, preferably from the group of the talcs, kaolin, loams, finely-pulverulent $SiO_2$, carbon and dextrins. The pulverulent carrier material, if present, amounts to preferably from 0.01 to 10% by weight. The pulverulent carrier material can be mixed with the insecticide mixture and the polymer by melt-kneading, but it is preferred first to mix the insecticide mixture and the pulverulent material and subsequently to mix this mixture with the polymer, for example by melt-kneading. It is especially preferred to use a mixture of the pulverulent material and the insecticide mixture for preparing a masterbatch.

Besides polymer, insecticide mixture and, if appropriate, pulverulent carrier, the polymer composition comprises, if appropriate, customary additives to thermoplastic molding compositions, such as pigments, antioxidants, lubricants and the like.

To produce the filaments according to these embodiments of the invention, a mixture is prepared of, for example, polymer, insecticide mixture and, if appropriate, further additives by melt-kneading, preferably at elevated temperatures, the mixture is extruded and the extrudate is processed to give pellets. Such pellets can be drawn by meltspinning, by the extrusion method, to give a filament from which nets according to the invention can be woven, for example by the Raschel method.

Details on netting material and its production for this embodiment of the invention are described for example in WO 2008/004711.

Net

Examples of suitable nets are textile materials, nontextile plastic materials, paper, leather, man-made leather, films and other, preferably flexible, materials.

The net employed preferably takes the form of a textile material. They can take the form of nets made of natural fibers or synthetic fibers. Of course, they can also take the form of mixtures of two or more different fibers. Examples of natural fibers comprise cotton fibers, jute fibers or linen fibers. Preferably, they take the form of synthetic fibers made of suitable polymers. Examples comprise polyamides, polyesters, polyacrylonitrile or polyolefins. Preferably, they take the form of polyamides, polyolefins and polyesters, especially preferably polyolefins, in particular polypropylene or polyethylene, and polyesters. Very especially preferred are polyester fibers, in particular polyethylene terephthalate (PET).

The fibers may take the form of monofilaments, oligofilaments or multifilaments, which may be smooth or textured.

Polypropylene and polyethylene may take the form of polypropylene or polyethylene homopolymers. However, they may also take the form of copolymers, which comprise small amounts of other comonomers in addition to the ethylene or propylene. Suitable comonomers may take the form of, in particular, other olefins such as, for example, ethylene or propylene and but-1-ene, but-2-ene, isobutene, pent-1-ene, hex-1-ene, hept-1-ene, oct-1-ene, styrene or α-methylstyrene, dienes and/or polyenes. In general, the comonomers in the polyethylene or polypropylene amount to no more than 20% by weight, preferably no more than 10% by weight. The nature and amount of the comonomers are selected by the skilled worker as a function of the desired fiber properties.

Products which are especially preferred for the production of fibers are relatively high-molecular-weight, viscous products which are characterized in the customary manner by their melt flow index (determined as specified in ISO 1133). Preferably, they may take the form of at least one polypropylene or polyethylene with a melt flow index MFR (230° C., 2.16 kg) of from 0.1 to 60 g/10 min. Preferably, they take the form of polypropylene with a melt flow index MFR (230° C., 2.16 kg) of from 1 to 50 g/10 min, especially preferably from 10 to 45 g/10 min and for example 30 to 40 g/10 min. Such types of polypropylene are particularly suitable for the production of fibers. Of course, a mixture of a plurality of different types of polypropylene may also be employed.

Depending on the nature of the net, the textile fibers have a thickness of from 0.05 to 0.6 mm, preferably 0.1 mm to 0.4 mm, especially preferably 0.12 to 0.35 mm and very especially preferably 0.2 to 0.3 mm.

The nets preferably have a mesh pattern with an even number of corners. In this context, the nets may consist preferably of a simple type of mesh only, for example of quadrangular meshes only or of hexagonal meshes only, or else they may also comprise two or more types of different meshes, for example a combination of octagonal and quadrangular meshes.

In this context, the meshes of the net should preferably be essentially of the same type, i.e. while the net may indeed feature minor deviations in respect of shape and size of the meshes, the values will not vary unduly around the means.

Suitable mesh sizes (length of the side of a square mesh) are in the range of 5 mm, preferably 2.5 mm, in particular 1.5 mm as the upper limit and 0.1 mm, preferably 0.25 mm, especially preferably 0.5 mm, in particular 0.7 mm as the lower limit.

The meshes of the net are preferably selected from the group of quadrangular, hexagonal or octagonal meshes.

The quadrangular meshes take the form of meshes in the shape of a parallelogram with the sides a and b. Naturally, the term "parallelogram" also comprises the terms "rectangle" and "square". The smaller angle between the two sides of the parallelogram will, as a rule, be between 60 and 90°. In the borderline case of 90°, the parallelogram takes the form of a rectangle. In the borderline case a=b and 90°, it takes the form of a square. The parallelogram furthermore has a height $h_a$. In the case of a rectangle or a square, the height $h_a$ corresponds to the length of side a. Square meshes are particularly preferred.

In the case of the hexagonal meshes, three pairs of sides a, b and c, which run in each case parallel to each other, are arranged at the distances $h_a$, $h_b$ and $h_c$. In the case of the octagonal meshes, four pairs of sides a, b, c and d, which run in each case parallel to each other, are arranged at the distances $h_a$, $h_b$, $h_c$ and $h_d$. A person skilled in the art knows that no continuous patterns can be established with octagons. A net which comprises octagonal meshes will, therefore, additionally comprise at least one second type of mesh. These may take the form of quadrangular meshes.

In a specific embodiment of the invention, the height $h_a$ in the parallelogram, the hexagon and the octagon is from 0.1 to 0.99 mm, preferably from 0.1 to 0.9 mm, especially preferably from 0.12 to 0.8 mm and very especially preferably from 0.25 to 0.7 mm.

In the parallelogram, the length-to-height ratio $b/h_a$ is from 1:1 to 5:1, preferably from 1:1 to 4:1 and especially preferably from 2:1 to 4:1. Therefore, in the case of a ratio $b/h_a$ of 1:1, the meshes may take the form of a square with a side length of from 0.1 to 0.99 mm. In the case of a wider ratio of $b/h_a$, they take the form of a structure which is elongated along one axis. By virtue of the distance $h_a$ of no more than 0.99 mm, even smaller insects are efficiently prevented from passing across the net, while the length can indeed be greater than 0.99 mm, so that the air permeability of the net is not unduly hindered.

In the case of a hexagon, the ratio $((h_b+h_c)/2)/h_a$ is from 1:1 to 5:1, preferably from 1:1 to 4:1 and especially preferably from 2:1 to 4:1. Here, the situation is analogous to the parallelogram. A ratio of 1:1 will result in a regular hexagon with three equal sides, each of which have an equal distance of no more than 0.99 mm to each other. A greater ratio $((h_b+h_c)/2)/h_a$ results in a hexagon which is elongated along one axis. The effect regarding permeability to insects and air is as in the case of the parallelogram.

In the case of an octagon, the ratio $((h_b+h_c+h_d)/3)/h_a$ is from 1:1 to 5:1, preferably from 1:1 to 4:1 and especially preferably from 2:1 to 4:1. Here, the ratios are analogous to the parallelogram. A ratio of 1:1 will result in a regular octagon with four equal sides, each of which have an equal distance of no more than 0.99 mm to each other. A greater ratio $((h_b+h_c+h_d)/3)/h_a$ results in an octagon which is elongated along one axis. The effect regarding permeability to insects and air is as in the case of the parallelogram.

Besides quadrangular and hexagonal meshes, it is also possible, for example, to employ combinations of quadrangular and octagonal meshes in this embodiment, or to vary the shape and size of the meshes in parts of the net. For example, the edges of the net can be knitted more densely, or else thicker textile fibers, which are also made of a different polymer, may be knitted in at certain distances in order to stabilize the net.

The terms "height" and "length" refer to the open area of each mesh without taking into consideration the fibers or the coated fibers. Analogously, the term "mesh size" for the purposes of the present invention means the hole size of the meshes, i.e. the open area of each mesh without taking into consideration the fibers or the coated fibers.

Textile net materials according to this embodiment of the invention are described in European Patent Application 08 161 456.

The thickness of the fibers used for the production of the textile material according to the invention, in particular of the nets according to the invention, is selected by the skilled worker depending on the desired properties of the net. As a rule, the thicker the fibers, the greater the mechanical stability of the net; on the other hand, the proportion of open area in comparison with the proportion of the fiber-covered area will decrease with decreasing mesh size. As a rule, the fiber thickness should be such that the open area of the net will be at least 20%, preferably at least 40% and in particular at least 50% of the net. Nets of the abovementioned type are commercially available.

The nets used can preferably take the form of single-layer nets. However, they may also take the form of what are known as spacer fabrics, where two nets are connected to one another with the aid of individual yarns to form a double layer.

The protective construction according to the invention is useful for any kind of stored goods susceptible to pest infestation, like food and other products obtained from plants such as coffee, dried fruits, cocoa, nuts, tea, cereals and spices. In a preferred embodiment it is used for protecting tobacco, tobacco bales or other tobacco products. It can be used for protecting any kind of tobacco, such as e.g. tobacco produced from *Nicotiana rostica* and *Nicotiana tabacum*, specifically dark tobacco, bright tobacco, burley tobacco, shade tobacco and Perique.

The construction is useful for protecting, the tobacco from any kind of pests encountered in the transport and storage of tobacco, specifically from storage pests, like bugs, beetles, moths and mites.

Such pests include:
Cigarette beetle (*Lasioderma serricorne*), tobacco moth (*Ephespha elutella*), confused flour beetle (*Tribolium confusum*), red flour beetle (*Tribolium castaneum*), saw-toothed grain beetle (*Oryzaephilus surinamensis*), yellow meal worm (*Tenebrio molitor*), lesser meal worm (*Alphitobius diaperinus*), granary weevil (*Sitophilus granarius*), lesser grain borer (*Rhyzopertha dominica*), maize weevil (*Sitophilus zeamais*), rice weevil (*Sitophilus oryzae*), angoumois grain moth (*Sitotroga cerealella*), Indian meal moth (*Plodia interpunctella*), drugstore beetle (*Stegobium paniceum*), cadelle beetle (*Tenebroides mauritanicus*), longheaded flour beetle (*Latheticus orizae*), dark mealworm (*Tenebrio obscurus*), dermestid beetles such as: black carpet beetle, larder beetle, wardrobe beetle, odd beetle, hide beetle, warehouse beetle, spider beetles, weevils, especially the bean weevil, grain mite, black flour beetle, flat grain beetles, fruit flies, vinegar flies, rusty grain beetle, hairy fungus beetle, flat grain beetle, sap beetles, deathwatch beetles, darkling beetles, and fungus beetles.

The construction according to the invention is specifically useful for the control of the cigarette beetle (*Lasioderma serricorne*), and the tobacco moth (*Ephespha elutella*), the two main pests in tobacco storage.

The invention is further illustrated by the following examples without limiting it thereby.

EXAMPLES

BRIEF DESCRIPTION OF THE DRAWINGS

FIG. 1*a* shows a support frame of the invention in bottom view,

FIG. 1*b* shows the support frame of the invention in top view,

FIG. 1*c* shows a further embodiment of the support frame.

FIGS. 2*a* and *b* show two embodiment of the joining element to join two frame sections of the support frame.

DETAILED DESCRIPTION OF THE DRAWINGS

Figure 3A:
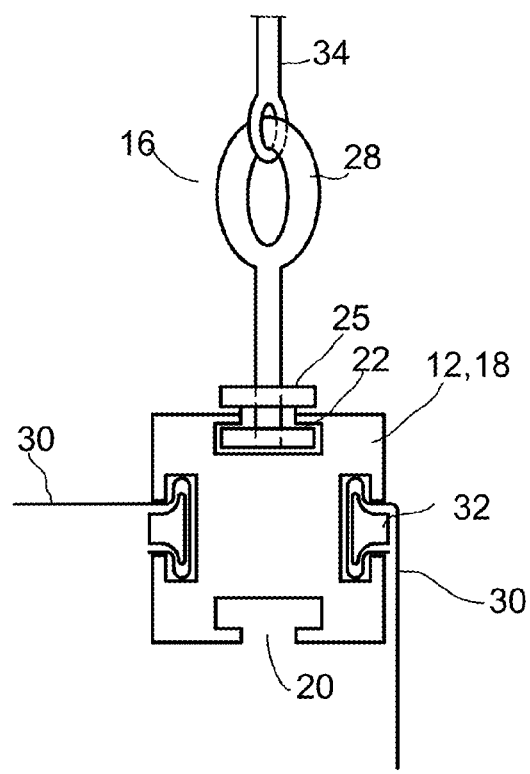
FIG. 3*a* and *b* shows a sectional view of an extruded section part.

FIG. 1*a* shows the bottom of a support frame 10 constructed using frame sections 12. The four shown frame sections 12 form a rectangular shaped frame. The frame sections 12 are held together by joining elements 14. In a preferred embodiment the joining elements 14 are constructed as corner brackets 26 and the frame sections 12 are formed by extruded section parts 18.

In this description a connecting element is an element to connect or join two parts by suitable means. These means comprise brackets, clamps, plates, bolts, screws and/or nuts.

A joining element is a connecting element adapted to join two frame sections 12 of the support frame 10.

A mounting element in this description is an element to fix a part to a structural element of the warehouse 1 by any suitable means. These means comprise brackets, clamps, plates, bolts, screws, nuts, hooks and/or rings.

A linking element in this description is an element to bridge the gap between two parts so that they can be joined by connecting elements. Suitable linking elements comprise ropes, chains, cables, beams, pillars and/or posts.

The term fastening element refers to an element adapted to fix a part to another part. Suitable fastening elements comprise screws, nuts, nails and/or glue.

FIG. 1*b* shows the support frame of FIG. 1*a* in top view. In the shown embodiment six connecting elements 16 are arranged on the support frame 10 to connect said support frame to means for suspending the support frame 35. The number of provided connecting elements 16 can vary depending on many parameters comprising the weight of the support frame 10, the weight of an attached net 30 and the load capacity of the wall/ceiling/floor of the warehouse 1.

In FIG. 1*c* another preferred embodiment of the support frame 10 is shown, wherein the support frame 10 comprises solid 12*a* as well as flexible frame sections 12*b*. The three flexible frame sections 12*b* are formed by ropes 19, the rigid frame section 12*a* is formed by an extruded section part 18. The joining elements 14 to join the different frame sections 12 comprise two rings 29, which join two flexible sections 12b formed by ropes 19, and hooks 28, which connect a flexible frame section 12b formed by a rope 19 to the rigid frame section 12a formed by the extruded section part 18.

In a further embodiment of the support frame 10 of the invention the support frame comprises three frame sections 12, forming a triangle.

In a further embodiment of the support frame 10 of the invention the support frame further comprises one or more curved frame sections 12.

In another embodiment of the invention, the support frame 10 comprises more than four frame sections 12, giving the support frame a polygonal shape.

FIG. 2a shows an embodiment of the joining element 14 constructed to join two frame sections 12 of the support frame 10. The two shown frame sections 12 of the support frame 10 are formed by extruded section parts 18. The extruded section parts 18 comprise slots 20 and are adapted two receive T-slot nuts 22. A corner bracket 26 is arranged on the two frame sections 12 and fixed to the extruded section parts 18 using screws 24 and the T-slot nuts 22. The area enclosed by the support frame 10 can be adjusted by moving the corner bracket 26 along one of the slots 20 before tightening the screws 24.

FIG. 2b shows another embodiment of the joining element 14 used to join two frame sections 12 of the support frame 10. The extruded section parts 18 which form the frame sections 12 comprising slots 20 on the four sides. One of the extruded section parts 18 is fitted with two T-slot nuts in the slot 20 facing the second extruded section part 18. The second extruded section part 18 is fitted with two fastening elements 23 in two slots 20 an alternate sides. The fastening elements 23 and the T-slot nuts are then joined using screws 24.

FIG. 3a shows a sectional view of an extruded section part 18 with connecting element 16 and attached nets 30. The extruded section part 18 comprises slots 20 on all four sides. The slot 20 on the top side of the extruded section part 18 receives the connecting element 16, comprising a T-slot nut 22, a hook 28, a nut 25 and a cable 34. The T-slot nut 22 is inserted into the slot 20 of the extruded section part 18 and receives the hook 28. The nut 25 secures the hook 28. The cable 34 is attached to the hook by knotting, welding, soldering, clamping or similar means. The nets 30 are attached and secured to the frame section 12 by insertion of the net 30 into the slot 20 together with a compression clamp 32. The compression clamp 32 releases the net 30 from the frame section 12, if the load on the net exceeds the clamping force of the compression clamp 32 thus an easy and effective protection is provided to protect the support frame 10 from structural collapse in case the net gets entangled.

Figure 3B:
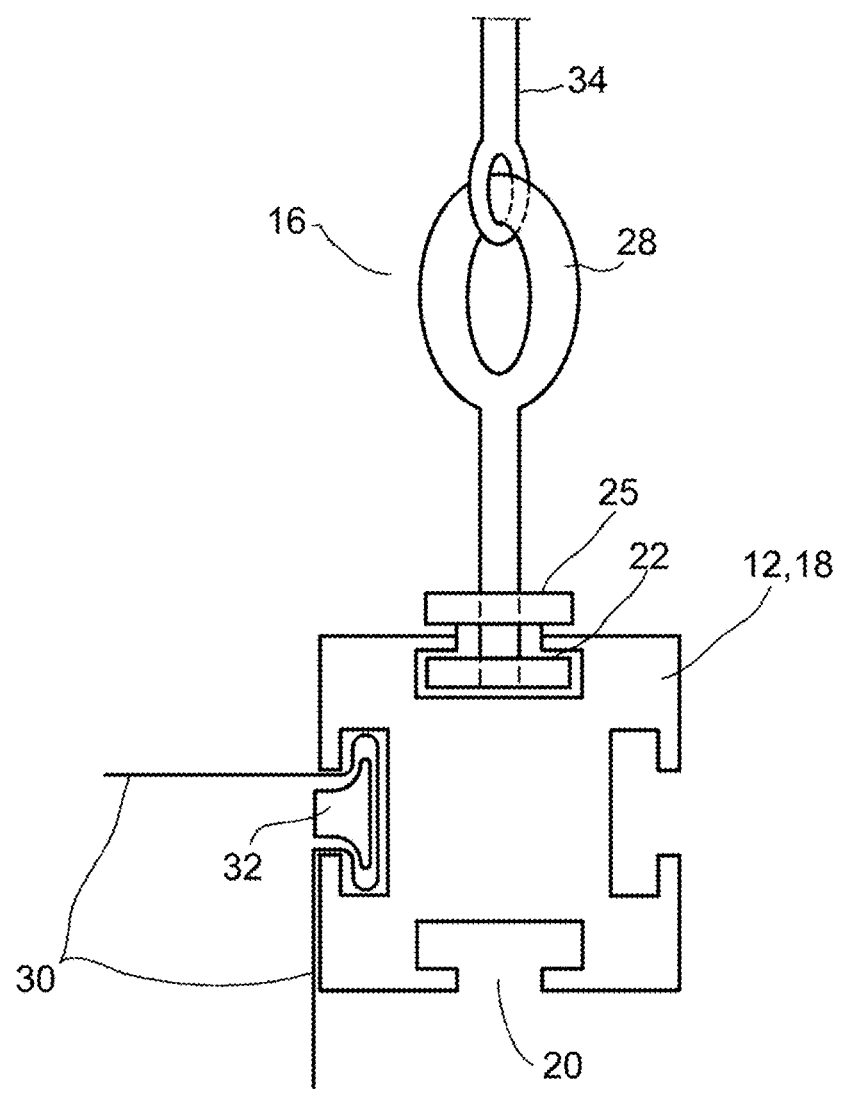

FIG. 3b shows the extruded section part 18 of FIG. 3a with a single three dimensional net attached. The extruded section part 18 comprises slots 20 on all four sides. The slot 20 on the top side of the extruded section part 18 receives the connecting element 16, comprising a T-slot nut 22, a hook 28, a nut 25 and a cable 34. The T-slot nut 22 is inserted into the slot 20 of the extruded section part 18 and receives the hook 28. The nut 25 secures the hook 28. The cable 34 is attached to the hook by knotting, welding, soldering, clamping or similar means. The single three dimensional net 30 is attached and secured to the frame section 12 by insertion of the net 30 into the slot 20 together with a compression clamp 32. The three dimensional net 30 covers the top and the four sides of the storage construction.

Figure 4A:
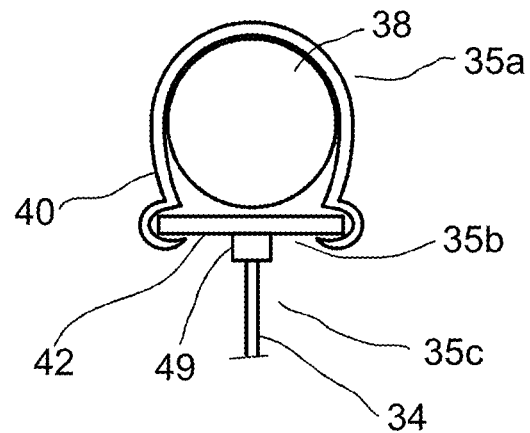
FIG. 4*a, b* and *c* show three different embodiments of the means for suspending the support frame.

FIG. 4a, b and c show three different embodiments of the means for suspending the support frame 35. These means as shown in FIG. 4 are attached to the ceiling 6 of a warehouse 1, but can also be used to suspend the support frame 10 from walls 5 of a warehouse 1. Which of these embodiments is preferred depends on the warehouse 1 and the structural elements used therein. The means 35 comprise essentially three components. The first is a suitable mounting element 35a to attach the means for suspending the support frame 35 to a structural element of the warehouse 1. The second and third parts are a connecting element 35b and a linking element 35c to attach the support frame 10. Depending on the mounting situation the means for suspension of the support frame 35 can comprise more than one of each element.

FIG. 4a shows an embodiment of the means for suspending the support frame 35 by attaching a clamp 40 with endplate 42 to a hollow section 38 of the structural elements of the warehouse 1. While in the embodiment shown in FIG. 4a the hollow section is of circular shape, the clamp 40 can be adapted fit hollow sections of any shape. A fastening element 49 is attached the endplate 42 and receives the cable 34. The cable 34 can then be attached to the connecting element 16 of the support frame 10.

Figure 4B:
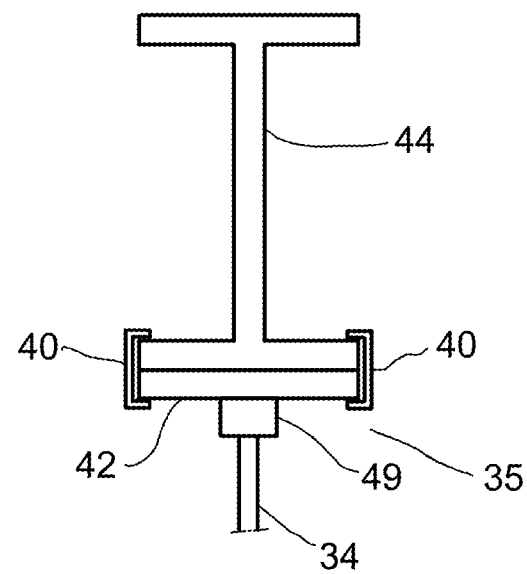

FIG. 4b shows another embodiment of the means for suspending the support frame 35 by attaching two or more clamps 40 to an I-beam 44 of the structural elements of the warehouse 1. The number of required clamps 40 varies depending on the load. The clamps secure an endplate 42 to the I-beam 44. The endplate 42 receives a connecting element 49 to attach the cable 34.

Figure 4C:
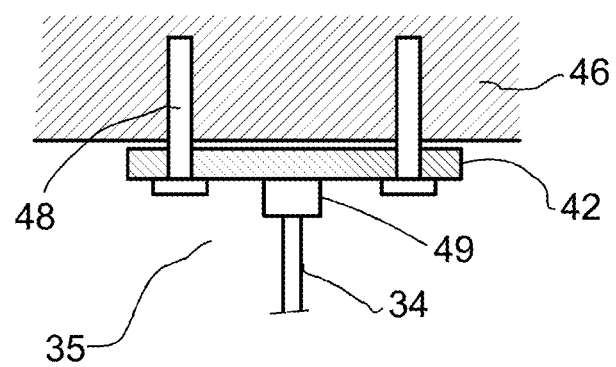

FIG. 4c shows another embodiment of the means for suspending the support frame 35 by attaching an endplate 42 to a concrete structure 46 of the warehouse 1. In the shown example bolts 48 are used as mounting elements to fix the endplate 42 to the concrete structure. The endplate 42 receives a connecting element 49 to attach the cable 34.

Figure 5:
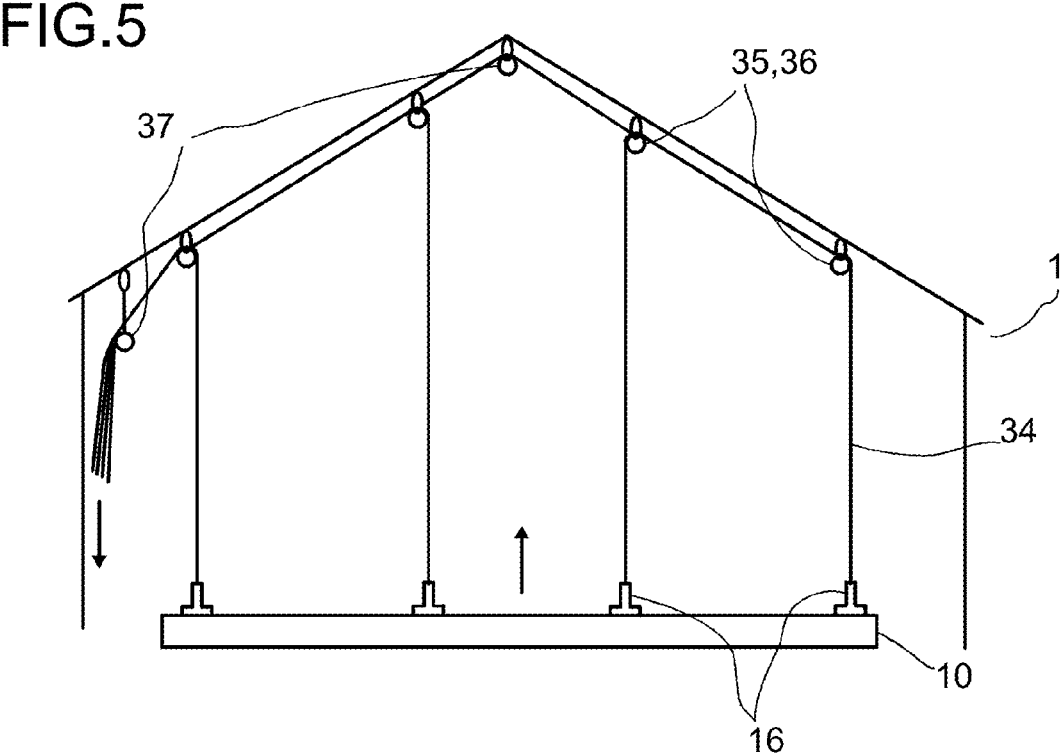
FIG. 5 shows an embodiment of the support frame in a suspended state.

FIG. 5 shows an embodiment of the support frame 10 in a suspended state and the means for suspending the support frame 35 of the invention. The means for suspending the support frame 35 are attached to the ceiling of the warehouse 1 and comprise pulleys 36 to receive the cables 34. The cables 34 are attached to the support frame 10 using the connecting element 16. Additional guide pulleys 37 are also attached to the ceiling 6. The cables 34 run up to the pulleys 36 of the means for suspending the support frame 35 and are guided back towards the ground using the guide pulleys 37. The support frame 10 can be lifted by pulling the cables 34. Once the support frame 10 is in the desired position, the cables 34 can be fixed using any suitable means to keep the support frame 10 in place.

Figure 6A:
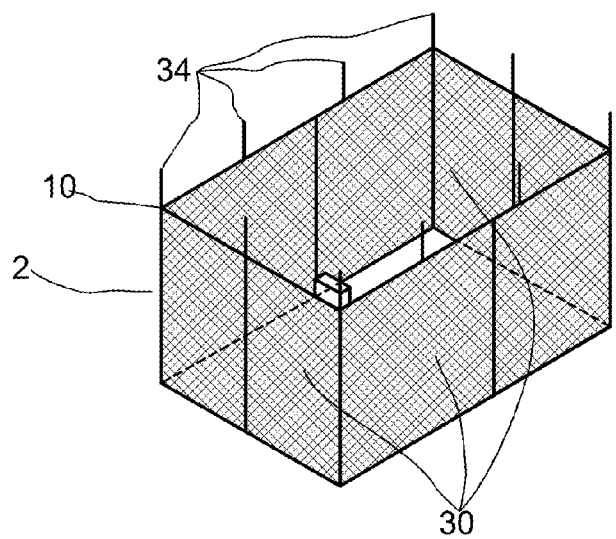
FIG. 6*a* shows a storage construction formed by the support frame in a suspended state with the nets attached.

FIG. 6a shows a storage construction 2 formed by the support frame 10 in a suspended state with the nets 30 attached. The support frame 10 is suspended from the ceiling using cables 34 attached to suitable means for suspending the support frame 35. Nets 30 are attached to all four sides of the support frame 10 and a net 30 covers the top of the support frame 10.

In a preferred embodiment of the invention a single three dimensional net 30 covers all four sides and the top of the support frame 10 without any gaps.

Figure 6B:
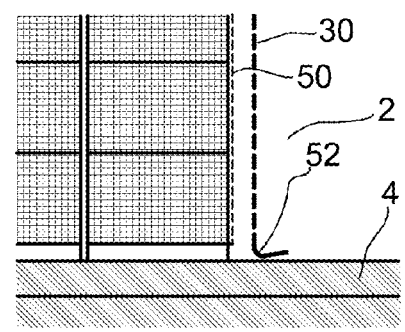
FIG. 6*b* shows the nets pooling on the floor.

In FIG. 6b a part of the storage construction 2 is shown. Goods 50 are placed inside the storage construction 2. One of the nets 30 is visible in FIG. 6b. The net 30 is attached to a side of the support frame 10. The size of the support frame is chosen so that the net 30 is not touching the goods 50. As can be seen in FIG. 6b, the length of the net 30 is larger than the height of the storage construction 2 so that a part 52 of the net 30 is pooling on the floor 4 of the warehouse 4.

Figure 7A:
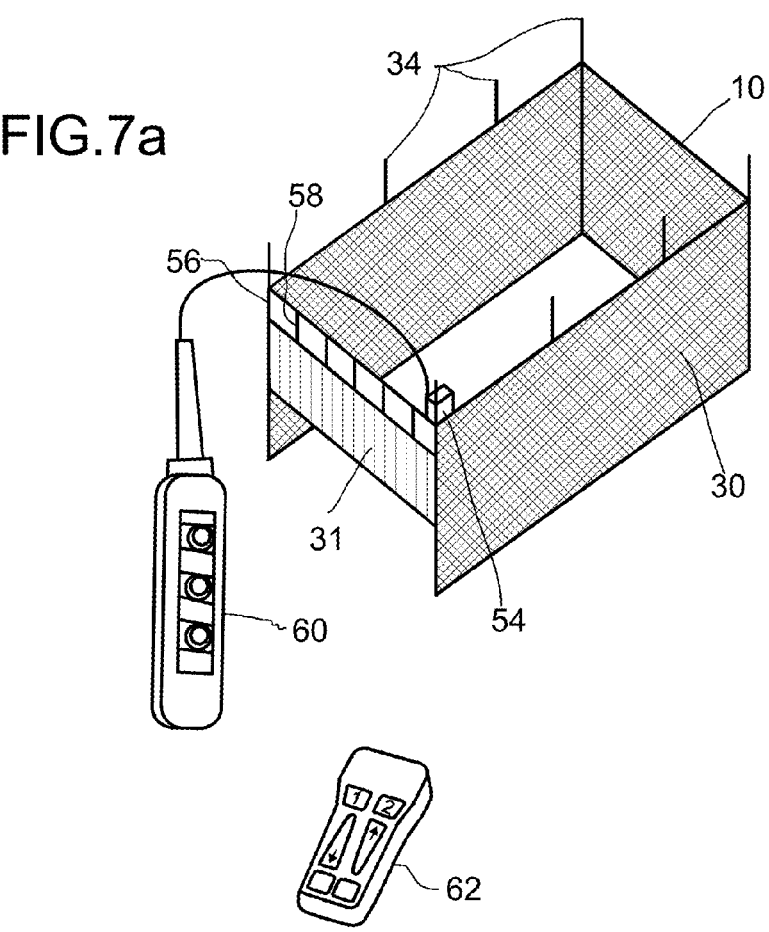
FIG. 7*a* shows an embodiment of the storage construction.

FIG. 7a shows an embodiment of the storage construction 2. Nets 30 are attached to all four sides of the support frame 10 and a net 30 covers the top of the support frame 10. The net 30 attached to the frame section 13 of the support frame 10 is partially lifted. The frame section 13 of the support frame 10 comprises means for opening and closing the net 31. These means include a motor 54, mounted on the frame section 13. The net 31 comprises ropes 58 which are connected to the motor 54 such that the motor 54 can lift and lower the net 31. In the shown embodiment the net 31 further comprises a pooling bar 56. The pooling bar 56 ensures that the net is lifted uniformly. If the net 31 comprises a sufficiently large number of ropes 58 the pooling bar 56 can be omitted. The motor 54 is controlled by remotes 60, 62. A wired remote 60 is suspended from the ceiling of the warehouse such that it can be operated by warehouse staff while on a forklift. Additionally wireless remotes 62 are also provided.

Figure 7B:
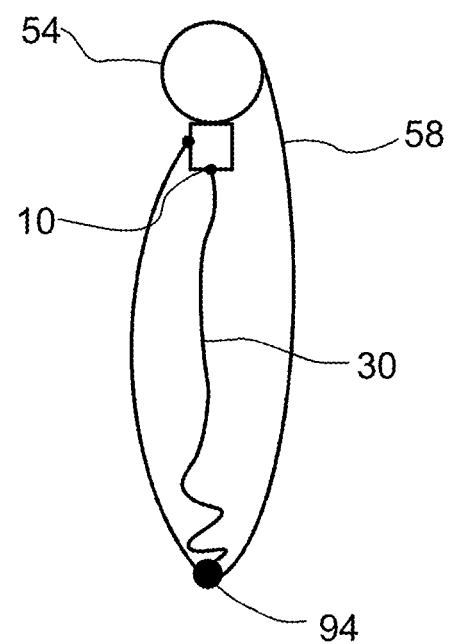
FIG. 7*b* shows a preferred embodiment of the opening mechanism.

FIG. 7b shows another embodiment of the invention where the ropes 58 are suspended from the support frame 10 and form straps which hold the net 30. In a preferred embodiment rollers 94 are attached to the ropes 58 as a weight. The net 30 can then be lifted by pulling on one end of the ropes 58 either manually or using a motor 54. Pulling on one side of the ropes 58 decreases the size of the straps thus lifting the net. This embodiment allows for an easier exchange of the net 30 as it does not require the ropes 58 to be fixed to the bottom of the net 30.

Figure 7C:
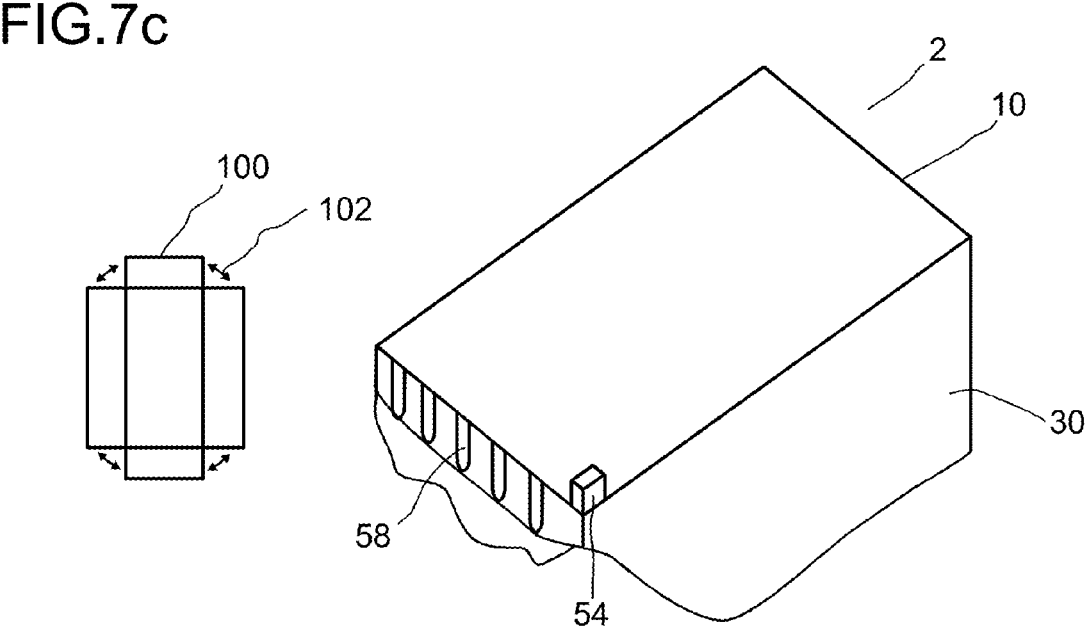
FIG. 7*c* and *d* show two embodiments of a three dimensional net.

FIG. 7c shows a storage construction 2 with a support frame 10 and a three dimensional net 30. The sewing pattern of the net 30 is shown with the reference numeral 100. The arrows 102 indicate the position of the seams. The net 30 has been lifted on one side of the storage construction 2 using ropes 58 and the motor 54.

As shown in FIG. 7c lifting the front side of the net 30 also affects the sides of the net 30 and no clear opening is formed.

Figure 7D:
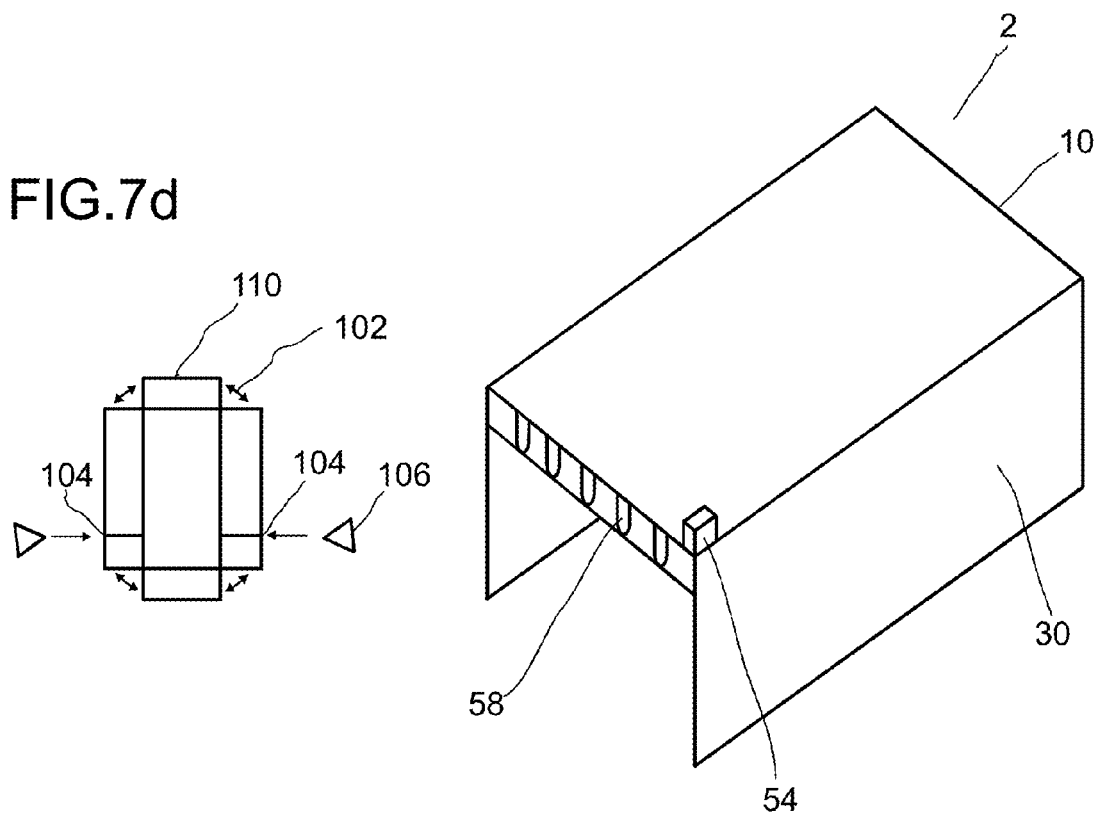

FIG. 7d shows a storage construction 2 with a support frame 10 and a three dimensional net 30. The sewing pattern of the net 30 is shown with the reference numeral 110. Here additional net material 106 is inserted into the three dimensional net at the positions 104. The positions 104 are located either at or near the seams 102 between the side to be opened by the means to open the storage construction 2 and the two adjacent sides. In the shown embodiment of the invention the additional net material 106 is of triangular shape. Further suitable shapes include rectangles, squares and segments of a circle.

As can be seen in FIG. 7d the additional net material 106 allows the net 30 to form a clean opening of approximately rectangular shape.

Figure 8A:
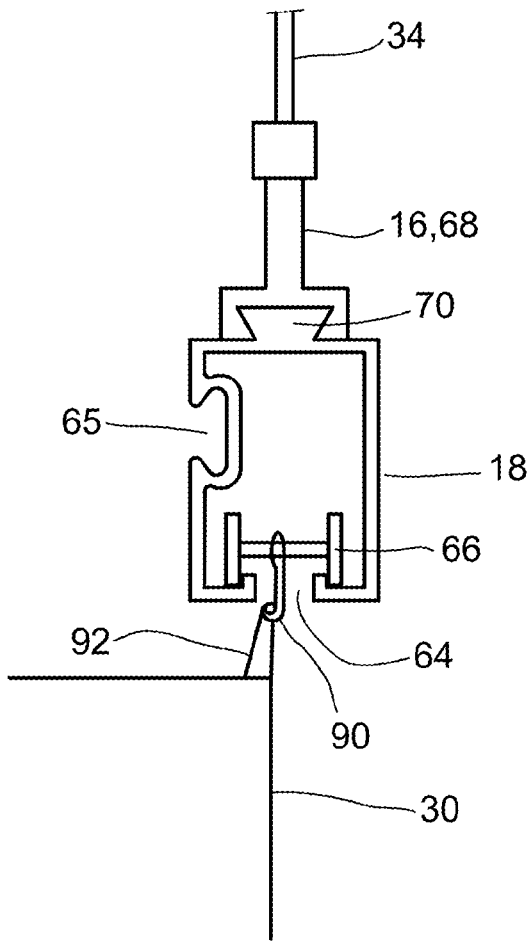
FIG. 8*a* and *b* show a further embodiment of the extruded section part.

FIG. 8a shows a further embodiment of the extruded section part 18. The extruded section part 18 is provided with a slot 65 on one side. On the lower side a slot 64 is arranged and the slot 64 receives a net 30 attached to rollers 66. The three dimensional net 30 is attached to the rollers 66 using straps 92 and hooks 90 attached to the rollers 66. The rollers 66 allow the net to be moved during installation and to be drawn similar to a curtain. On the top side of the extruded section part 18 a bracket 68 is attached using a dovetail connection 70. The bracket 68 receives the cable 34 which connects to the means for suspending the support frame 35.

Figure 8B:
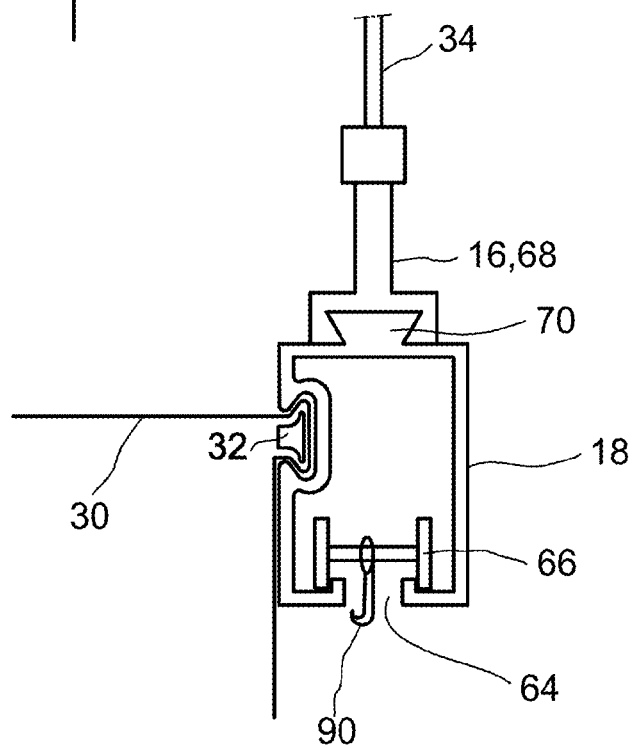

FIG. 8b shows the extruded section part 18 with the net 30 completely installed. The three dimensional net 30 has been moved into the correct position using the rollers 66. In order to reduce the sagging of the net 30 it is preferred to tighten the net 30 by inserting the net 30 into the slot 64 of the extruded section part 18. The compression clamp 32 keeps the net 30 in the tightened position.

Figure 9:
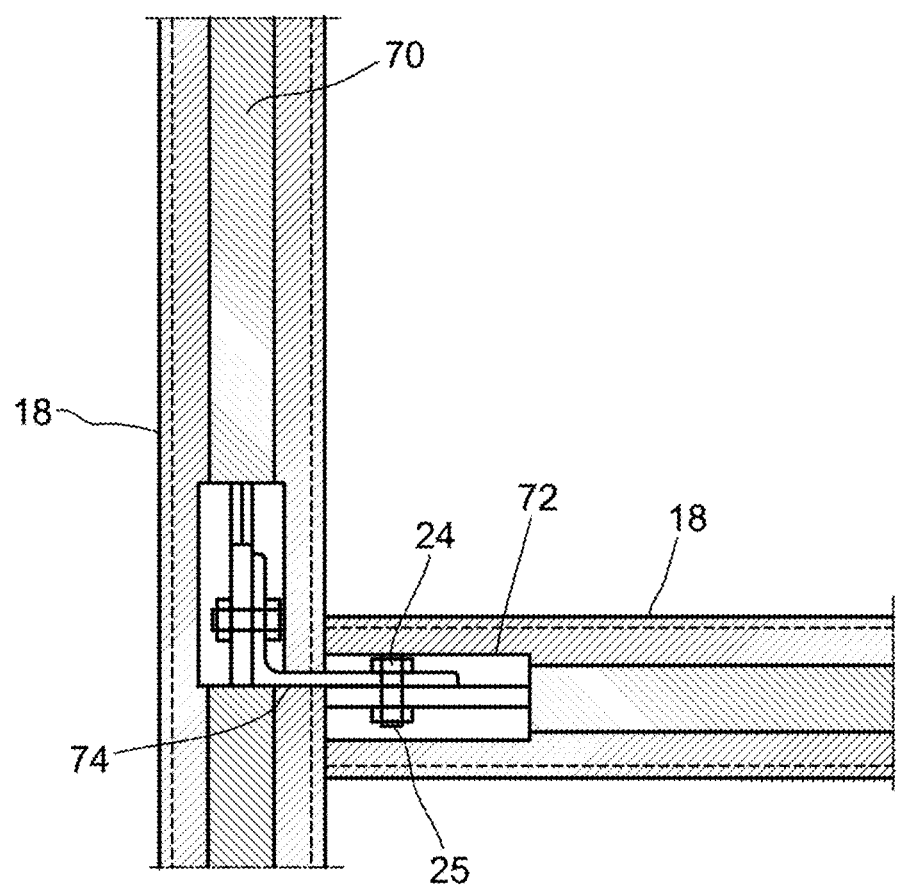
FIG. 9 shows another embodiment of a joining element adapted to join two extruded section parts of a support frame.

FIG. 9 shows another embodiment of a joining element 14 adapted to join two extruded section parts 18 of a support frame 10. The top side of the section parts 18 is provided with dovetail connections 70 to receive brackets 72. The two brackets 72 are then joined using an angle bracket 74 and suitable fastening means, e.g. screws 24 and nuts 25.

FIG. 10 shows the deployment of the nets 30 on a support frame 10 as shown in FIGS. 8 and 9. The nets 30 are already attached to the support frame 10 and the support frame 10 is in a suspended state.

Figure 10A:
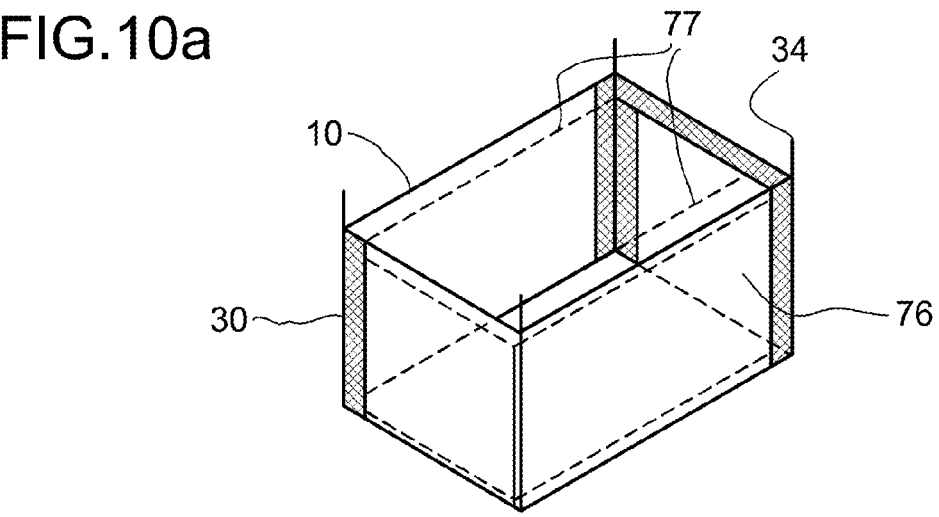
FIG. 10 shows the deployment of the nets on a support frame.

FIG. 10a shows the storage construction 2 with support frame 10 and all nets 30 completely retracted. The nets 30 on the four sides of the storage construction 2 are attached to rollers 66 which are received by slots 64 of the extruded section parts 18 forming the support frame 10. The net 30 covering the top of the support frame 10 is inserted into the slot 65 of one of the extruded section parts 18 of the support frame 10.

Figure 10B:
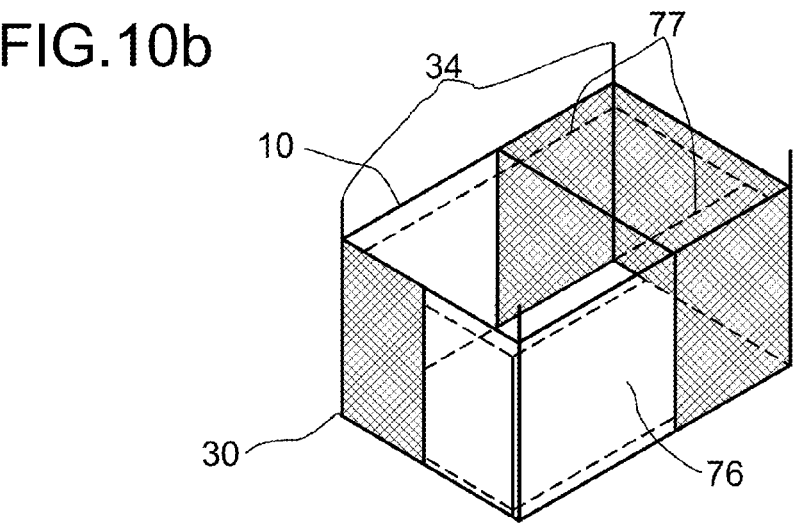

FIG. 10b shows the deployment of the nets. The nets 30 on the side of the storage construction 2 can be drawn similar to curtains. The arrow 76 indicates the direction of deployment of the nets 30. The net 30 covering the top of the support frame 10 further comprises guide ropes 77 which span from the extruded section part 18 to which the net 30 is attached to the extruded section part 18 on the opposite side of the support frame 10. The guide ropes 77 aid in the deployment phase of the net 30 by supporting and guiding the net 30.

Figure 10C:
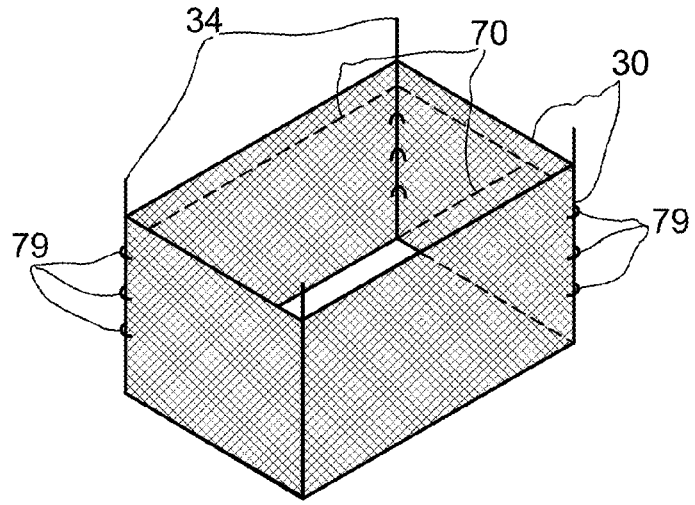

FIG. 10c shows the storage construction 2 with support frame 10 and the nets 30 completely deployed. The net 30 covering the top of the support frame 10 is now fastened to all four extruded section parts 18 of the support frame 10 using compression clamps 32.

The net 30 on one side of the storage construction 2 can be opened by drawing the net similar to a curtain. The parts of the net 30 which need not to be opened are further connected to each other using clamps 79.

In a further embodiment of the invention, one of the frame sections 12 of the support frame 10 comprises a motor 54 for automation of the opening and closing of the nets.

Figure 11:
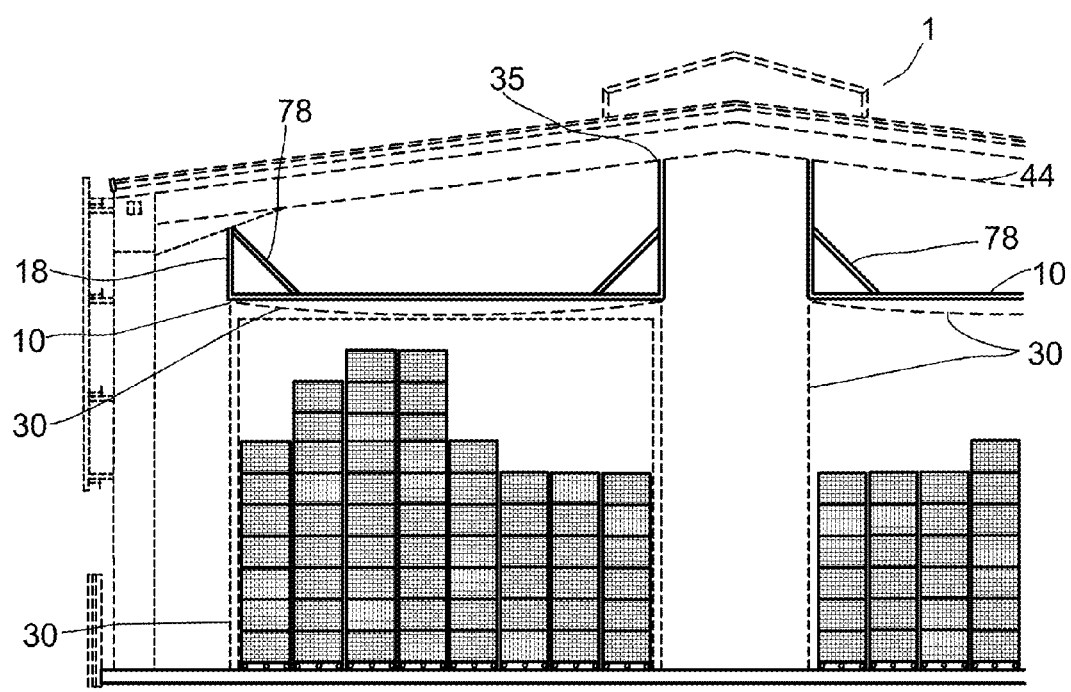
FIG. 11 shows a further embodiment of the support frame.

In FIG. 11 another embodiment of the invention is shown. The support frame 10 is connected to the means for suspending the support frame 35 using extruded section parts 18. Cross beams 78 are provided for additional strength.

Figure 12:
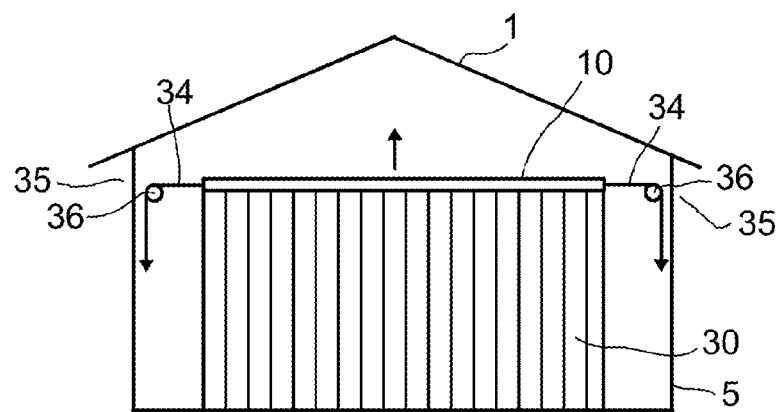
FIG. 12 shows another embodiment of the support frame in a suspended state.

FIG. 12 shows a further embodiment of the invention. The support frame 10 is suspended from the side walls 5 of the warehouse 1 using means for suspending the support frame 35 adapted to be fixed to the walls 5. The support frame 10 is connected to the means for suspending the support frame 35 by cables 34 and pulleys 36. The support frame 10 is lifted by pulling the cables 34. The support frame 10 is then fixed in the desired height by securing the cables 34.

FIG. 13 shows a support frame 10 comprising two rigid frame sections 12a and two flexible frame sections 12b. The support frame 10 is suspended by means for suspending the support frame 35. The means for suspension 35 are adapted to be placed on the floor 4 of the warehouse 1. The means for suspension 35 is constructed as a foldable stand 80 comprising feet 81 and hinges 82 and posts 83. In the shown embodiment the foldable stand 80 contains four extruded section parts 18 as posts 83, one for each corner of the support frame 10. Each of the four posts 83 is mounted to a foot 81 using a hinge 82. The hinge 82 allows the posts 83 to swivel and thus the folding of the foldable stand 80.

Figure 13A:
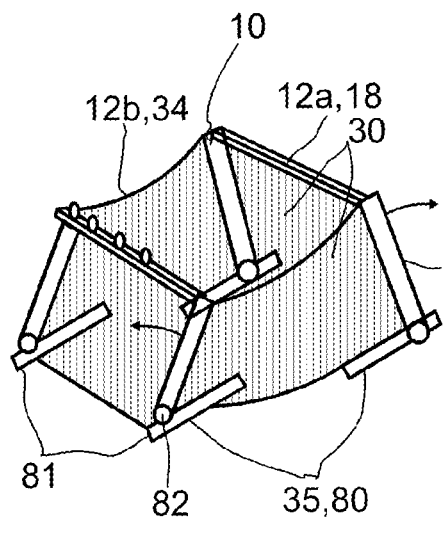
FIG. 13 shows an embodiment of the storage construction comprising suspending means adapted to be fixed to the floor.

FIG. 13a shows the erection of the stand 80 with the support frame 10. In one embodiment of the invention, the nets 30 are attached to the support frame 10 before the stand 80 is erected. In another embodiment of the invention the nets 30 are attached to the support frame 10 after the stand 80 is erected. Each of the two rigid frame sections 12a of the support frame 10 is mounted on two posts 83 of a foldable stand 80. The two rigid frame sections 12a are connected to flexible frame sections 12b to form the support frame 10. The flexible frame sections 12b allow the support frame 10 to be folded while mounted to the foldable stand 80. The support frame is located on the floor 4 of the warehouse 1 while the foldable stand 80 is in a folded state. To suspend the support frame 10 the posts 83 of the stand 80 are erected. The support frame 10 is lifted and the flexible sections 12b of the support frame 10 are spanned. In a preferred embodiment of the invention the stand 80 is secured to the base of the warehouse by suitable means. Suitable means comprise bolts, clamps and/or screws.

Figure 13B:
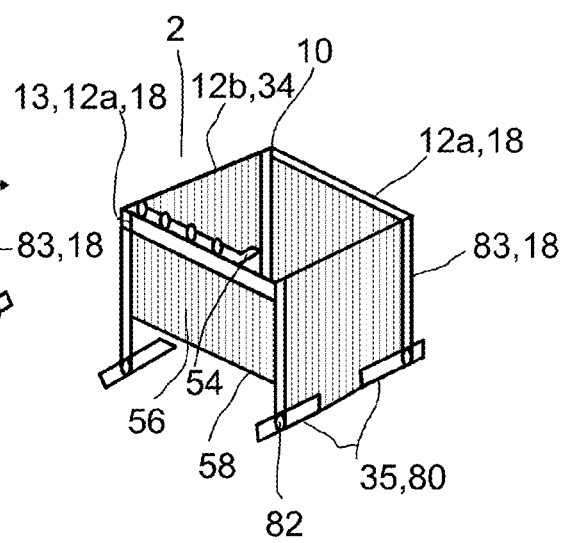

FIG. 13b shows the erected state of the stand 80. The hinges 82 of the stand are fixed to hold the posts 83 in an essentially vertical state and the feet 81 are secured to the floor of the warehouse 1 by suitable means. The support frame 10 with the rigid frame sections 12a and the flexible frame sections 12b are suspended by the support stand 80 and holds nets 30. One net 30 is attached to each of the four sides of the support frame 10 and one net 30 covers the top of the support frame 10. The assembled and erected storage construction 2 comprises the stand 80, support frame 10 and the net 30. The net 30 attached to the frame section 13 is provided with ropes 58 and a pooling bar 56 such that the net 30 of the frame section 13 can be lifted by the motor 54.

In another preferred embodiment of the invention the stand 80 comprises inflatable posts 80 instead of hinges. This greatly reduces the weight of the stand 80 and allows for a quick installation procedure by inflation of the posts 80 using compressed air.

Figure 14:
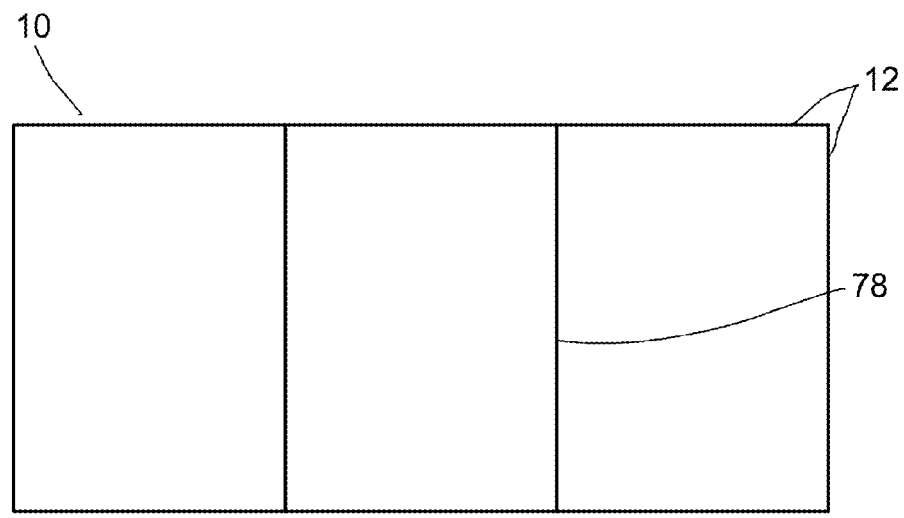
FIG. 14 shows a further embodiment of the support frame comprising cross beams.

FIG. 14 shows another embodiment of the support frame 10 of the invention. The support frame 10 comprises cross beams 78 in addition to the frame sections 12. The added cross beams 78 increase the strength and rigidity of the support frame 10 so that a larger load can be supported and so that unwanted movements of the support frame 10 are reduced.

Figures 15A, 15B:
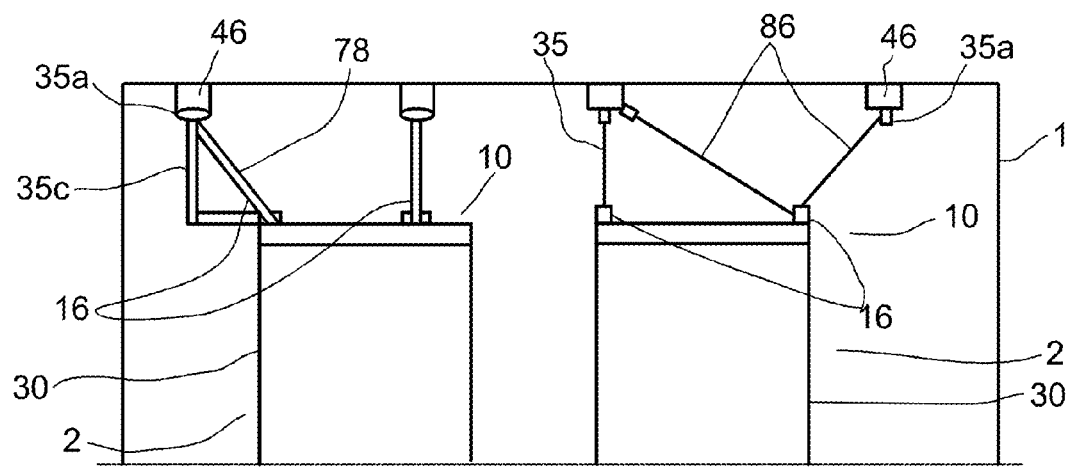
FIG. 15 shows further embodiments of the means for suspending the support frame.

FIG. 15a shows another embodiment of the means for suspending the support frame 35. The desired position of the support frame 10 is not located directly under the structural elements 46 of the warehouse 1. The means for suspending the support frame 35 are attached to the concrete structure 46 of the ceiling 6 of the warehouse 1 by suitable mounting means 35a. The support frame 10 is attached using extruded section parts 18 as linking element 35c. Cross bars 78 in the linking element 35c allow the suspension of the support frame 10 in the shown position. Preferably the means for suspending the support frame 35 are arranged so that the load on the ceiling does not exceed 2 kg/m$^2$.

FIG. 15b shows another embodiment of the means for suspending the support frame 35. Similar to the situation shown in FIG. 15a, there are no suitable structural elements 46 of the warehouse 1 located above the desired position of the support frame 10. The means for suspension 35 comprise cross cables 86 to allow the suspension of the support frame 10 in the shown position.

Figure 16:
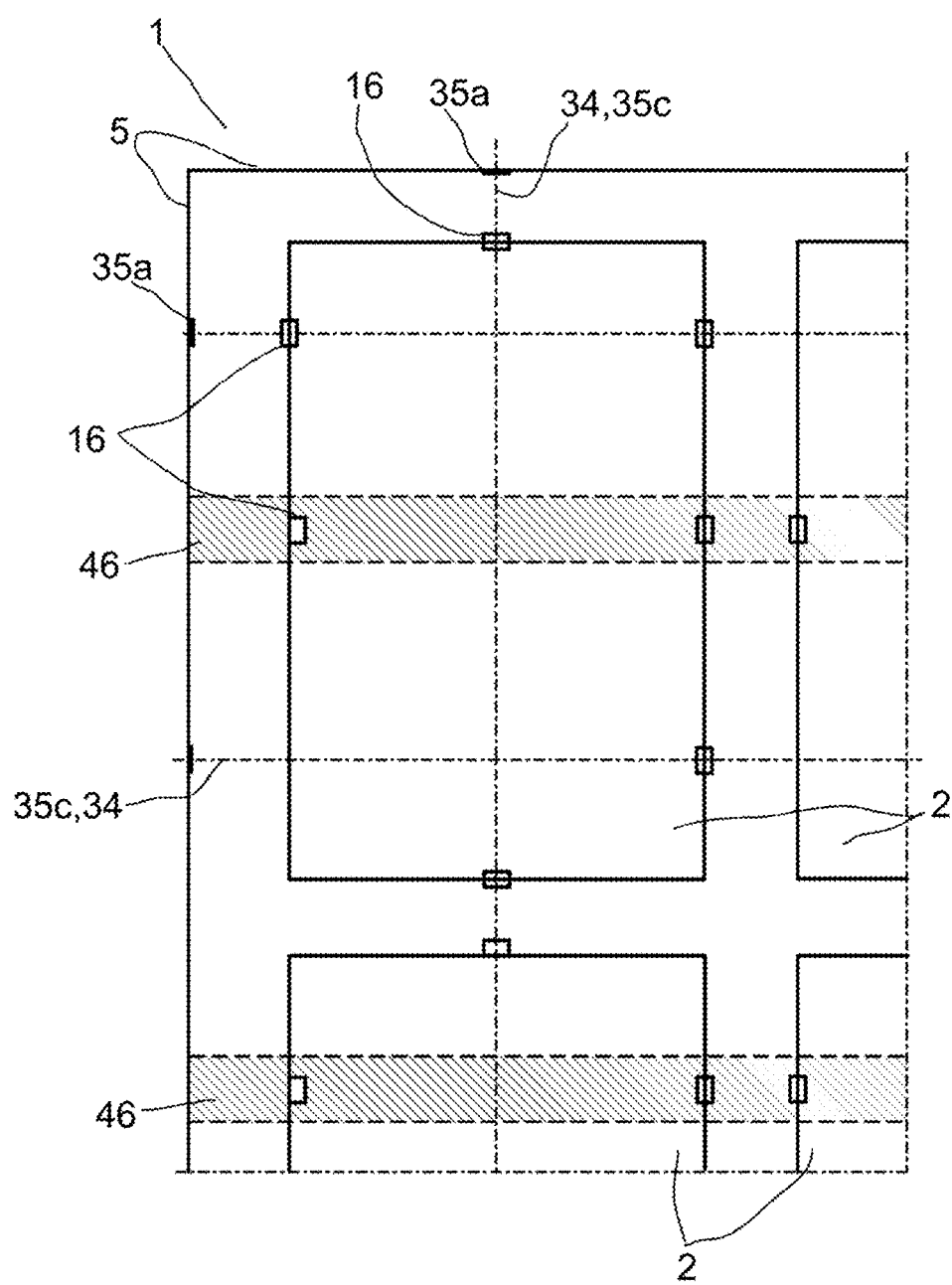
FIG. 16 shows a schematic view of the layout of the warehouse with several storage constructions.

FIG. 16 shows a schematic view of the layout of the warehouse 1 with several storage constructions 2. The ceiling 6 of the warehouse 1 comprises several concrete structures 46. The spacing of the concrete structures 46 as shown in FIG. 16 is too large to allow the suspension of the support frames 10 in the desired positions using only means for the suspension of the support frame 35 adapted to be fixed to the ceiling 6 of the warehouse 1. FIG. 16 further shows means for suspension 35 with mounting elements 35a adapted to be fixed to the walls 5 of the warehouse 1. The linking element 35c shown in FIG. 16 spans the entire length of the warehouse 1 and is mounted to the opposite wall by a second mounting element 35a. Connecting elements 16 connect the support frame 10 to the linking elements 35c.

FIG. 17 shows two further embodiments of a rigid frame section 12 of the support frame 10 of the invention.

Figure 17A:
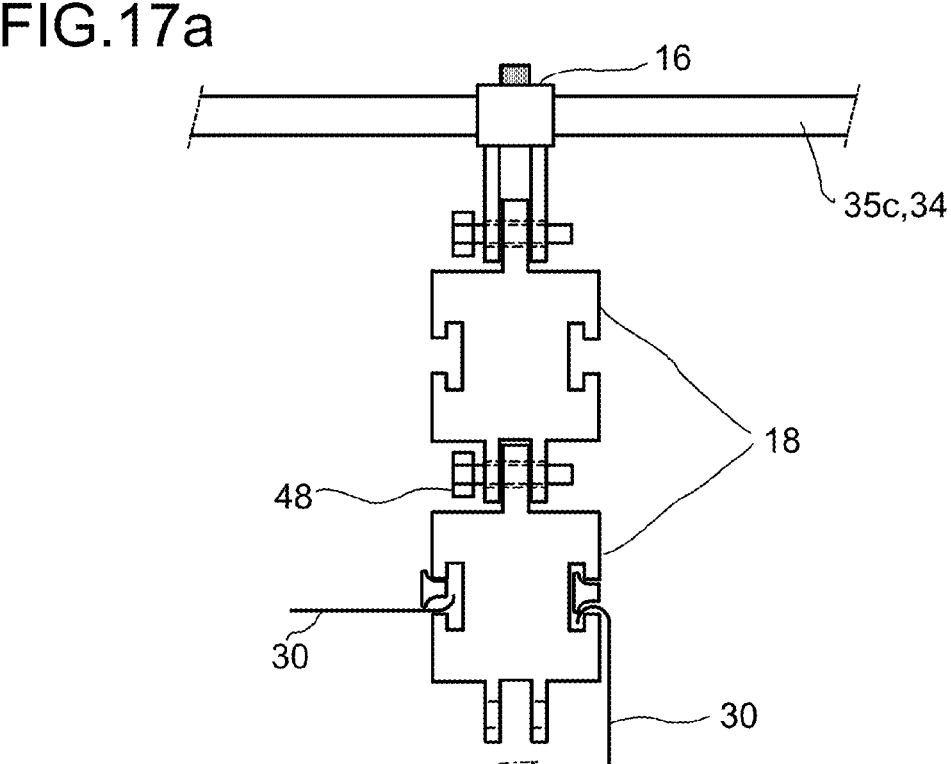
FIGS. 17*a* and *b* show two further embodiments of a rigid frame section of the support frame of the invention.

In FIG. 17a a rigid frame section 12 is formed by stacking two extruded section parts 18. The two extruded section parts 18 are joined by suitable connecting elements 48. A connecting element 16 connects the frame section 12 to the linking element 35c of the means for suspending the support frame 35. The nets 30 are attached to the extruded section part 18 using compression clamps 32. The frame section 12 possesses increased strength compared to a frame section made up from a single extruded section part 18. The load capacity and the distance that can be spanned by the frame section 12 are increased.

Figure 17B:
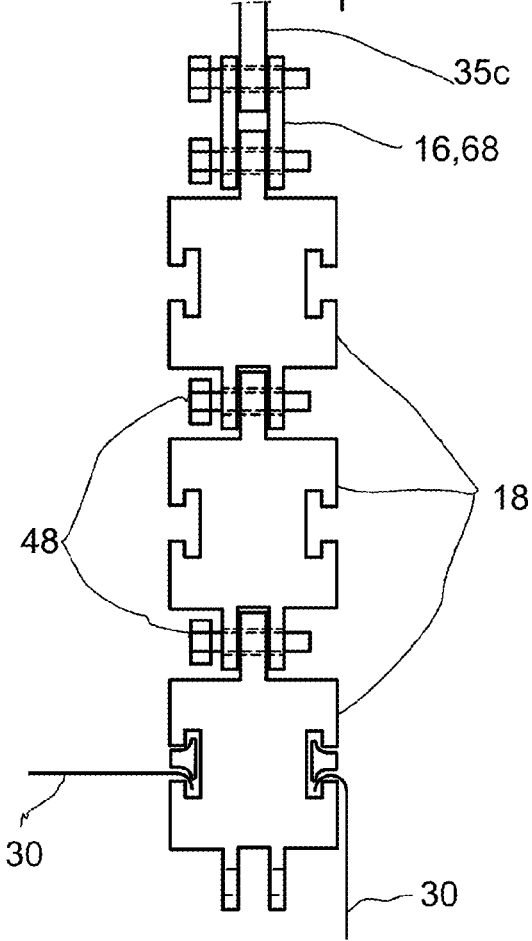

In FIG. 17b a rigid frame section 12 is formed by stacking three extruded section parts 18. The three extruded section parts 18 are joined by suitable connecting elements 48. A connecting element 16 connects the frame section 12 to the linking element 35c of the means for suspending the support frame 35. The nets 30 are attached to the extruded section part 18 using compression clamps 32. The maximum load capacity and maximum distance that can be spanned by the frame section 12 is further increased.

The invention claimed is:

1. A system for protecting stored goods in a storage room, comprising one or more storage constructions formed by one or more pesticide treated nets, capable of enclosing the stored goods,
    wherein the storage construction further comprises a support frame,
    means for suspending the support frame,
    wherein the system further comprises
    means for opening and closing at least one section of the storage construction while the support frame is in a suspended state,
    and means for avoiding an overall structural collapse of the storage construction if a net gets entangled and the forces exerted onto the net exceed a certain maximum load of the support frame or means for suspending the support frame wherein the means for avoiding an overall structural collapse are adapted to fix the net to the support frame such that the means for avoiding an overall structural collapse releases the net from the support frame if the pull on the net exceeds the certain maximum load of the support frame or means for suspending the support frame, wherein the storage room has a floor, and wherein the one or more nets are pooling on the floor of the storage room.

2. The system of claim 1, wherein the means for suspending the support frame are adapted to
    affix the support frame to the ceiling of the storage room, and comprise mounting means to affix the suspending means to the ceiling and/or support structure of the storage room and connecting elements to connect the support frame to the mounting means, or
    affix the support frame to at least two walls of the storage room, and comprise mounting means to affix the suspending means to the walls and connecting elements to connect the support frame to the mounting means, wherein the mounting means comprise clamps, brackets and/or bolts, or be placed and/or fixed on the floor of the storage room, and constructed as a stand comprising rigid beams and connecting elements to receive the support frame, wherein the connecting elements comprise rigid beams, ropes, cables, chains and/or pulleys, wherein the ropes, cables and/or chains are provided with tensioning elements and wherein the connecting elements are fixed to the support frame using fastening elements.

3. The system of claim 1, wherein the pesticide is an insecticide.

4. The system of claim 1, wherein the storage construction further comprises four sides and a top and wherein one net is employed which is a single three dimensional net forming all four sides and the top of the storage construction.

5. The system of claim 1, wherein the net comprises seams between the section to be opened and two adjacent sides and wherein additional net material is inserted as an intermediate portion at the seams between the section to be opened and closed and the two adjacent sides.

6. The system of claim 1, wherein the one or more nets comprise a weighted rope.

7. The system of claim 1, wherein the support frame is composed of one or more sections and each section comprises rigid beams, ropes, cables and/or chains and wherein each section provides means to fasten the one or more pesticide treated nets comprising guide ropes, clamps, slots, bolts, hooks and/or rollers, wherein the support frame further comprises joining elements to join the sections of the frame, and wherein the support frame comprises connecting elements to connect the support frame to the means for suspending the support frame.

8. The system of claim 7, wherein at least one section of the support frame comprises rigid beams which are extruded section parts.

9. The system of claim 1, wherein the means for opening and closing the at least one section of the storage construction comprise a motor and means to control the motor.

10. The system of claim 9, wherein the net on the at least one section of the support frame is provided with ropes that are arranged such that they can be pulled by the motor wherein the ropes extend to the bottom of the net or wherein the ropes are suspended from the support frame and form straps which hold the net.

11. The system of claim 9, wherein the means to control the motor is one of a wired remote, a RF or IR wireless remote or a motion sensor.

12. The system of claim 1, wherein the means for avoiding an overall structural collapse are one or more of Velcro strips, compression clamp strips, holding clamps, bolts or hooks provided with breaking points.

13. The system of claim 1, further comprising means to monitor pest infections.

14. A method for protecting stored goods in a storage room, comprising the steps of installing the system of claim 1 in a storage room and placing the goods inside the storage construction.

15. The method of claim 14, wherein the net on at least one section of the support frame is provided with means for opening and closing the storage construction and wherein the storage construction is opened before moving/removing goods into or out of the storage construction and closed afterwards.

16. The method of claim 15, wherein the means for opening and closing the storage construction comprise a motion sensor and wherein an opened section of the storage construction is automatically closed if the motion sensor does not detect any motion during a predetermined time span.

17. The method of claim 14, wherein pest levels are monitored and wherein the one or more nets are renewed if the pest levels are rising.

* * * * *